Figure 1:
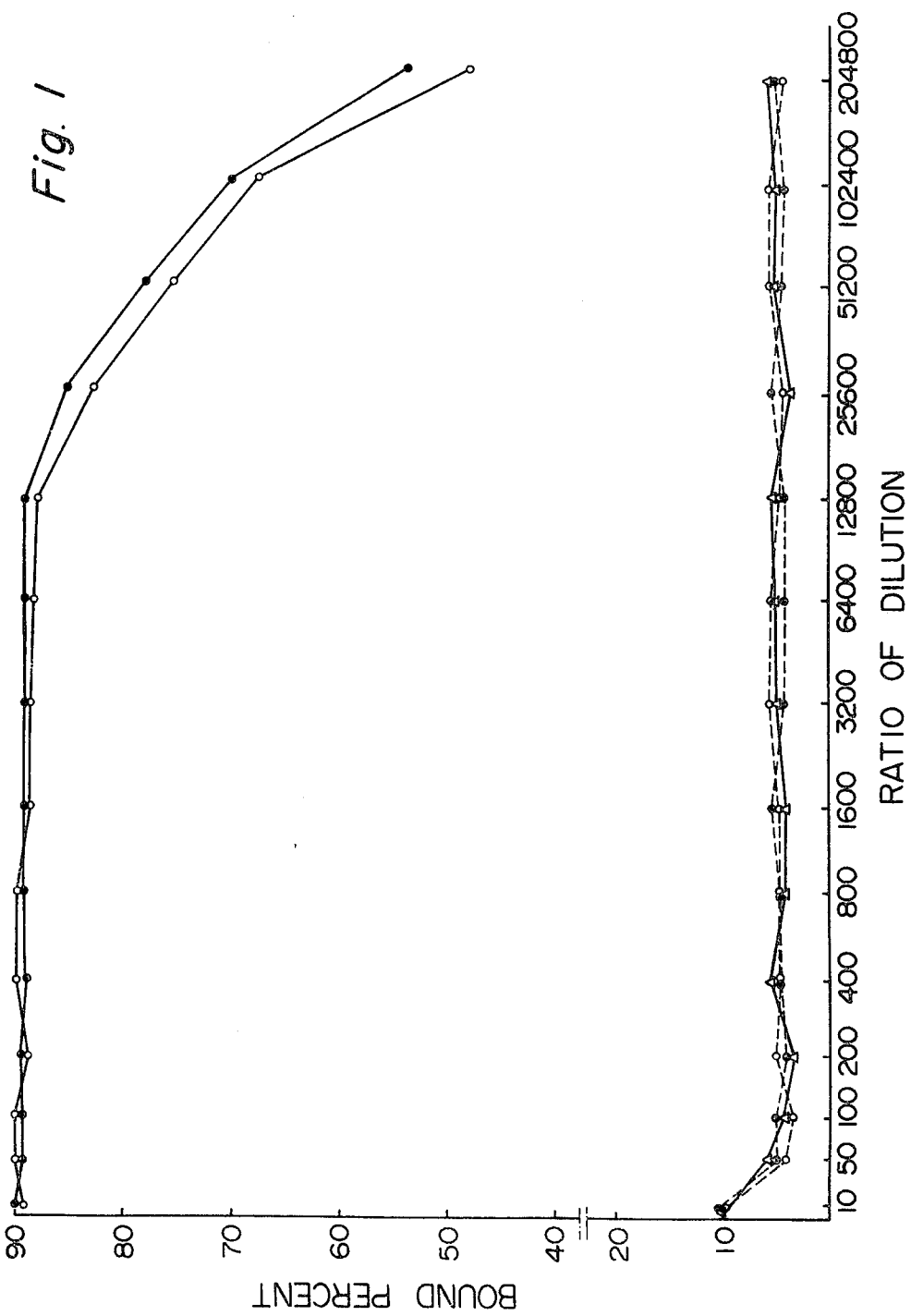

United States Patent [19]
Sakakibara et al.

[11] 4,341,758
[45] Jul. 27, 1982

[54] IMMUNOCHEMICAL ASSAY REAGENT FOR THE DETERMINATION OF HAPTENS, AND ASSAY METHOD THEREWITH

[75] Inventors: Kyoichi Sakakibara, Tokyo; Hideaki Manita, Sagamihara; Masaaki Gondo, Kawasaki; Haruo Yamashita, Kunitachi, all of Japan

[73] Assignee: Teikoku Hormone Mfg. Co., Ltd., Tokyo, Japan

[21] Appl. No.: 83,938

[22] Filed: Oct. 11, 1979

[30] Foreign Application Priority Data

Oct. 14, 1978 [JP] Japan .................. 53-125710
Oct. 14, 1978 [JP] Japan .................. 53-125711

[51] Int. Cl.³ ............................ G01N 33/54
[52] U.S. Cl. .................... 424/12; 23/230 B; 424/8; 424/13; 424/78; 424/81
[58] Field of Search ............ 424/8, 12, 13, 78, 81, 424/82, 83; 23/230 B; 260/6, 7, 8

[56] References Cited

U.S. PATENT DOCUMENTS

| | | | |
|---|---|---|---|
| 3,502,545 | 3/1970 | Westman | 424/12 X |
| 3,857,931 | 12/1974 | Hager | 424/12 |
| 4,035,316 | 7/1977 | Yen | 424/12 X |
| 4,060,597 | 11/1977 | Sato | 424/12 X |
| 4,119,590 | 10/1978 | Seita | 260/8 |

FOREIGN PATENT DOCUMENTS

| | | |
|---|---|---|
| 2743445 | 3/1978 | Fed. Rep. of Germany . |
| 7729186 | 9/1977 | France . |
| 53-41420 | 4/1978 | Japan . |

OTHER PUBLICATIONS

Erlanger, J. of Biol. Chem., vol. 228, 1957, pp. 713-727.
Erlanger, J. of Biol. Chem., vol. 234, 1959, pp. 1090-1094.
Linder, Steroids, vol. 19, 1972, pp. 357-375.
Spector, Science, vol. 168, Jun. 12, 1970, pp. 1347-1348.
Tulchinsky, J. of Clin. Endocrin. & Metab., vol. 33, 1971, pp. 775-782.
Gross, Steroids, vol. 18, 1971, pp. 555-563.
Kellie, J. of Steroid Biochem., vol. 3, 1972, pp. 275-288.
Cheng, Febs Letters, vol. 36, Nov. 1973, pp. 339-342.
Inayama, Chem. Pharm. Bull., 1977, pp. 838-840.
Molday, J. of Cell Biol., vol. 64, 1975, pp. 75-88.

*Primary Examiner*—Anna P. Fagelson
*Attorney, Agent, or Firm*—Wenderoth, Lind & Ponack

[57] ABSTRACT

Novel immunochemical assay reagents comprising combinations of (A) a carboxyl-containing water-soluble mono-olefinic polymeric compound combined with a hapten or its chemically modified product, or a hapten-supported latex resulting from the chemical linking of the hapten-bound polymeric compound to a polymeric latex, with (B) a hapten antibody, or a hapten antibody-supported carrier; and a method for immunochemically determining haptens by using the aforesaid reagent. This reagent is very stable and can be stored for an extended period of time without degradation. It enables transition from an agglutination inhibited pattern to an agglutinated pattern to be discerned clearly and rapidly with high sensitivity.

6 Claims, 1 Drawing Figure

IMMUNOCHEMICAL ASSAY REAGENT FOR THE DETERMINATION OF HAPTENS, AND ASSAY METHOD THEREWITH

This invention relates to stable immunochemical assay reagents for haptens and to an assay method using these reagents.

Methods have long been known for determining traces of biologically active substances existing in body fluids such as blood or urine by immunochemical techniques. For example, there is a method which comprises sensitizing erythrocytes or red cells with an antigen or antibody, and reacting the sensitized erythrocytes with an antibody or antigen existing in a body fluid of a given subject, thereby inducing immunochemical agglutination or an agglutination inhibiting reaction. In another known method, non-biological particles such as a synthetic resin latex, bentonite, collodion, cholesterol crystals and quartz are used as a solid carrier in immunochemical reactions instead of the erythrocytes.

In connection with such immunochemical assay methods, it is known to use as a kind of hapten antigen a hapten-carrier linked material obtained by chemically binding a steroid, a kind of hapten, with a lysine residue of a protein through an amide linkage (Journal of Biological Chemistry, Vol. 228, pages 718–727, 1957).

A method is also known to determine a steroid in an assay sample immunochemically by using both an antibody obtained by immunizing a mammal with an antigen protein having a free amino group to which a steroid, a kind of hapten, is linked, and a carrier sensitized with a steroid protein complex obtained by linking a protein other than the aforesaid antigen protein to the aforesaid steroid (see Japanese Laid-Open Patent Publication No. 123819/75).

Recently, there was suggested an immunochemical assay method for the determination of haptens which involves the use of both an antibody-sensitized carrier obtained by sensitizing a carrier with a hapten antibody, and a hapten-carrier linked material obtained by linking a hapten capable of reacting with the hapten antibody to an antigenic carrier or a carrier sensitized with this linked material (see Japanese Laid-Open Patent Publication No. 41420/78).

Since a hapten cannot produce an antibody by itself when it is used singly to immunize an animal, it is the usual practice to render the hapten capable of producing an antibody by linking an antigenic substance such as proteins or polysaccharides to the hapten and then immunizing an animal with the linked product under proper condition. Hence, a reagent resulting from the linking of a protein or polysaccharide to the same hapten is used as an antigen. In such a case, however, the stability of the reagent is reduced because the protein or the like linked to the hapten is denatured, decomposed, or putrefied. It is necessary therefore to store the reagent at low temperatures or under ice cooling, and various difficulties are encountered particularly during long-term storage.

It is an object of this invention therefore to provide a method which can rapidly determine traces of haptens existing in blood, urine and other body fluids with high sensitivity by an immunochemically reproducible and stable operation. We have now found that the above object can be achieved very effectively by using an immunochemical assay reagent comprising a carboxyl-containing water-soluble mono-olefinic polymeric compound combined with a hapten or its chemically modified product, or a latex (having a particle diameter from about 0.01 to about 2 microns) linked to the carboxyl-containing water-soluble mono-olefinic polymeric compound combined with a hapten (hapten-holder).

To the best of the knowledge of the present inventors, it has not been known heretofore to use such a reagent in the immunochemical assay of haptens.

In the immunochemical determination of haptens present in body fluids using the reagent of this invention, it is possible to use both this reagent and any antibody capable of reacting with the aforesaid reagent or a carrier sensitized or chemically combined with the antibody, and to determine an agglutination inhibiting reaction between the two.

We have found however that haptens can be determined advantageously with higher sensitivity within shorter periods of time by a stable operation by using (A) a hapten-holder, or a hapten-holder linked latex resulting from the chemical linking of a carboxyl-containing water-soluble mono-olefinic polymeric compound combined with a hapten or its chemically modified product to a latex having a particle diameter of about 0.01 to about 2 microns, and (B) a hapten antibody, or a hapten antibody-supported latex or a hapten antibody-supported carrier comprising a latex having a particle diameter of about 0.01 to about 2 microns sensitized or chemically combined with the hapten antibody or a carrier sensitized or chemically combined with the hapten antibody, and by determining the agglutination inhibiting action of the two reagents (A) and (B) due to the hapten in a body fluid of a given subject.

The present invention is described in greater detail below.

Haptens

The "haptens", as used in the present invention, denote low-molecular compounds which are not antigenic by themselves, but which show antigenicity when bound to antigenic substances, for example antigenic high-molecular compounds such as proteins and polysaccharides, and have reactivity with antibodies formed by immunizing animals with such antigenic substances. Components existing in animals including physiologically active substances and metabolites thereof and drugs administered and metabolites thereof are especially important haptens to which the present invention is applicable. Specific examples of the haptens are given below.

(I) Steroidal haptens (i) Estrogens such as estrone, estradiol, estriol, estetrol, equilin and equilemin.

(ii) Natural gestagens which are produced in animals or exist as metabolites, such as progesterone, pregnanediol and pregnanetriol, and synthetic gestagens such as 19-norethisterone, and chlormadinone acetate.

(iii) Androgens such as testosterone, dehydroepiandrosterone, dihydrotestosterone, androsterone and etiocholanolone.

(iv) Corticoids such as cortisol, cortisone, deoxycorticosterone, aldosterone, tetrahydroaldosterone and tetrahydrocortisol.

(v) Other steroids such as vitamin D derivatives; bile acids such as cholic acid, desoxycholic acid and chenocholic acid; cardenolides; saponins; and sapogenins.

(II) Haptens of biologically active amines (i) Catecholamines and their metabolites, such as epinephrine, norepinephrine, dipamine and ephedrine.

(ii) Bislogically active alkaloids such as morphine, codeine, heroin, morphine glucuronide, cocaine, mescaline, papaverine, narcotine, yohinbine, reserpine, ergotamine and strychnine.

(iii) Amine drugs such as LSD, amphetamine, meprobamate and metamphetamine.

(III) Other haptens

Low molecular peptides which do not act as antigens, such as TRH and LH-RH; thyroid hormones such as diiodothyronine, triiodothyronine and thyroxine; prostaglandin derivatives such as prostaglandin $E_2$, prostaglandin $E_3$, and prostaglandin $F_{1\alpha}$; vitamins such as vitamin A, vitamin B derivatives (for example vitamin $B_1$, $B_2$, $B_6$, and $B_{12}$, vitamin E and vitamin K; antibiotics such as penicillin derivatives, actinomycin, chloromycetin and tetracycline.

The haptens contemplated by this invention, however, are not limited to these specific examples.

Chemical Modification of Haptens

In the present invention, the haptens are chemically combined with carboxyl-containing water-soluble mono-olefinic polymeric compounds (to be referred to as "holder" for convenience) either directly or after they have been chemically modified.

Various methods have been known to modify haptens chemically. In the present invention, any modifying methods can be employed which chemically bind the haptens to the functional groups (e.g., carboxyl or hydroxyl) of the holders. Especially preferred methods for chemically modifying haptens are those which introduce a carboxyl group, a primary amino group, a secondary amino group, or a hydroxyl group, above all the carboxyl group or the primary amino group, into haptens. Some examples are described below.

A carboxyl group can be introduced into a hapten having a carbonyl group by converting it to the corresponding carboxymethyl oxime (for example, Journal of Biological Chemistry, Vol. 234, pages 1090–1094, 1959). Or the hapten may be brominated, and then reacted with thioglycolic acid to introduce a carboxyl group into it (for example, Steroids, Vol. 19, pages 357–375, 1972).

It is known that reduction of an oxime of a carbonyl compound yields a primary amino compound. This product can also be utilized as a chemically modified product of hapten.

A hapten having a hydroxyl group can be modified by reacting it with monochloroacetic acid to form the corresponding carboxymethyl ether (for example, Science, Vol. 168, pages 1347–1348, 1970), or reacting it with succinic anhydride to form a hemisuccinate (for example, Journal of Clinical Endocrinology, Vol. 33, pages 775–782, 1971).

A carboxyl group may be introduced into a hapten having a phenolic hydroxyl group by coupling a paracarboxybenzene diazonium salt with the ortho- or para-position to the hydroxyl group of the hapten (for example, Steroids, Vol. 18, pages 555–563, 1971).

With regard to glucuronides which are metabolites of steroids, their carboxyl groups can be utilized (for example, Journal of Steroid Biochemistry, Vol. 3, pages 275–288, 1972). If these carboxyl groups cannot be directly utilized, they may be converted to amino compounds by reaction with suitable diamine derivatives.

Haptens having a secondary amino group can be converted to primary amine derivatives by, for example, alkylating the amino group thereof with N-protected aminoalkylhalogen compounds, and then splitting off the protective group (for example, FEBS Letters, Vol. 36, pages 339–342, 1973). Or a carboxyl group can be introduced into such haptens by reaction with bromoacetic esters followed by hydrolysis (for example, Chemical and Pharmaceutical Bulletin, Vol. 25, pages 838–840, 1977).

Haptens which do not have suitable functional groups may first be subjected to such means as hydroxylation by microorganisms, and then to the aforesaid methods to introduce the desired functional groups.

Holders

The holders, used in this invention may be any carboxyl-containing water-soluble mono-olefinic polymeric compounds. The term "water-soluble", used herein, means that when at least 1 part by weight of such a polymeric compound is dissolved in 1000 parts by weight of distilled water, a clear solution forms. So long as the solubility of the polymeric compound is above the lower limit specified, it may be as high as is desired. The polymeric compound may have a weight average molecular weight of about $10^3$ to $10^7$ or higher. Usually, those having a weight average molecular weight of some ten thousand to several million can be suitably used. These polymeric compounds may have a hydroxyl group as a functional group in addition to the carboxyl group. These functional groups are involved in chemical binding to the functional groups of haptens or their chemically modified products or to the functional groups of latices to be described hereinbelow, and also serve to impart water solubility to these polymeric compounds as holders.

The polymeric compounds used as holders in this invention are considered to be biologically inactive substances, and generally do not have antigenicity.

Examples of these polymeric compounds include homopolymers or copolymers of acrylic acid or methacrylic acid, a copolymer of maleic acid and vinyl acetate or a saponification product thereof, copolymers of maleic acid with vinyl alcohol, lower alkylvinyl ethers, acrylic acid, lower alkyl acrylates, methacrylic acid, or lower alkyl methacrylates, and hydrolysis products of these copolymers. These polymeric compounds may also be a copolymer of acrylic acid or methacrylic acid with beta-hydroxyethyl acrylate or acrylamide, or a terpolymer containing the aforesaid monomers as structural units.

Chemical Binding of Haptens or Their Modified Products to Holders

Preferably, the chemical binding of haptens or their chemically modified products to holders is carried out through an amide or ester linkage, especially through an amide linkage. This binding can be effected by using a known amide linkage reaction or ester linkage reaction as described below.

For example, when a hapten or its chemically modified product (to be inclusively referred to as "hapten") contains an amino group and the holder contains a carboxyl group, or vice versa, the hapten can be chemically bound to the holder through an amide linkage by any of the following methods.

Methods For Binding Haptens to Holders Through an Amide Linkage

(1) Carbodiimide Method

This method comprises forming an amide linkage between the amino group and the carboxyl group by dehydrocondensation. This can be achieved by adding an amount of a carbodiimide compound which is required for the desired binding or is slightly in excess of it to a solution of the two compounds, and reacting them at room temperature or under ice cooling. The carbodiimide compound itself changes to a urea derivative.

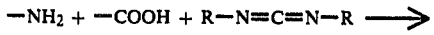

Any reaction solvent can be used which does not have a functional group that will participate in the reaction. For example, there can be used ethyl acetate, tetrahydrofuran, dioxane, dimethylformamide, and chloroform as the reaction solvent. The reaction solvent may contain any desired proportion of water, and the reaction may be performed in aqueous solution. When the reaction is to be carried out in an organic solvent, dicyclohexylcarbodiimide is most frequently used as the carbodiimide compound. In a reaction in a water-containing solvent, a water-soluble carbodiimide such as 1-ethyl-3-(3-dimethylaminopropyl)carbodiimide hydrochloride may be used.

(2) Carbonyl Diimidazole Method

This method, like the carbodiimide method, comprises inducing dehydrocondensation between the amino group and the carboxyl group. It can be performed by adding a required amount of carbonyl diimidazole to a solution of the two components. Since this reagent is sensitive to moisture and immediately decomposes upon contact with water, it is preferred to use a solvent which does not contain water.

(3) Mixed Acid Anhydride Method

The carboxyl group forms a mixed acid anhydride with, for example, a chloroformic acid ester in the presence of an organic base. The mixed acid anhydride readily reacts with the amino groups to form an amide linkage.

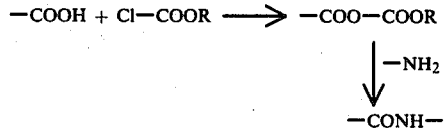

Examples of the chloroformate are lower alkyl esters (e.g., ethyl, iropropyl or isobutylesters) of chloroformic acid, and isobutyl chloroformate is most frequently used. Tertiary amines such as triethylamine or N-methylmorpholine are used as the organic base.

The same reaction solvents as described hereinabove with regard to the carbodiimide method can be used. Since the mixed acid anhydride is unstable in water, care must be taken not to use hydrous materials in the formation of the mixed acid anhydride. The reaction temperature during the formation of the mixed acid anhydride is about −10° C. to −20° C., and after adding the amino compound, the reaction is continued at room temperature. Water or a water-containing solvent may be used when the amino compound is added.

(4) Active Ester Method

The theory of the active ester method is that when the carboxyl group is converted to an ester of a compound having a great electron attracting property, the electron density on the carbonyl group decreases and consequently the carbonyl group attacks a functional group having a high basicity such as an amino group to form an amide linkage. Examples of the active ester include esters of phenol derivatives such as para-nitrophenol, 2,4-dinitrophenol, pentachlorophenol, thiophenol, naphthol and 3-hydroxyquinoline, esters of N-hydroxy compounds such as N-hydroxysuccinimide and N-hydroxypiperidine, and alkyl esters such as cyanomethyl. The same solvents as described above with regard to the carbodiimide method can be used.

(5) Azide Method

Conversion of a carboxyl compound to an ester and subsequent reaction with hydrazine affords an acid hydrazide. By the action of nitrous acid, the acid hydrazide is converted to an acid azide which reacts with the amino group to form an amide linkage.

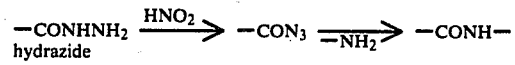

Specifically, the amide linkage can be formed by a classical method which comprises reacting hydrazide with sodium nitrite in dilute hydrochloric acid, isolating the resulting acid azide, and then reacting it with an amine compound in a suitable organic solvent; or a method which comprises treating hydrazide with an alkyl nitrite such as t-butyl nitrite or i-amyl nitrite in the presence of hydrogen chloride in an organic solvent (which may contain water) to form an acid azide, and without isolating the acid azide, reacting the resulting product with an amine compound.

(6) Acid Chloride Method

The most common method comprises converting a carboxyl compound into an acid chloride, and reacting it with an amino compound to form an amide linkage. Conversion to the acid chloride may be performed by a direct method which comprises reacting the carboxyl compound with phosphorus pentachloride, thionyl chloride, phosphorus oxychloride, etc., or an exchange reaction method which comprises reacting the carboxyl compound with oxalyl chloride. The reaction of the acid chloride with the amino compound can be performed by the "Schotten-Baumann method" which comprises performing the reaction in water while adding an alkali, or a method which comprises performing the reaction in an inert solvent such as benzene in the presence of an organic base such as pyridine or triethylamine.

(7) DPPA Method

There can also be employed a method which comprises adding diphenylphosphroyl azide (DPPA) to a solution of a carboxyl compound and an amino compound, and then adding an organic base such as triethylamine or N-methylmorpholine to form an amide linkage. In this method, dimethylformamide can be conveniently used as a solvent. The reaction temperature may be from that attained under ice cooling to room temperature.

The chemical bonding can be effected by any of the above methods (1) to (7). However, any method which requires severe conditions should be avoided in the present invention because haptens may be unstable depending upon their other substituents. The carbodiimide method (1) and the DPPA method (7) can be used most suitably. To a solution of the holder and a suitable amount of a hapten is added an equimolar amount or slightly excessive amount, to the hapten, of a carbodiimide or DPPA, and they are reacted (in the case of DPPA, an organic base is added further prior to the reaction). After the reaction, the entire reaction mixture is dialyzed against water in a cellophane tube whereupon the unreacted hapten and reagent and by-products are driven to the external solution. Concentration or lyophilizing of the dialyzate affords the desired hapten (or modified product thereof)-holder bound product.
[Method for binding haptens to holders through an ester linkage]

When the hapten or its chemically modified product has a suitable reactive hydroxyl group and the holder has a carboxyl group, or vice versa, the hapten can be chemically bound to the holder through an ester linkage.

When the hapten or its chemically modified product has a hydroxyl group and the holder has a carboxyl group, the carboxyl group is reacted with, for example, thionyl chloride to form an acid chloride and then reacted with the hapten to form a hapten-holder bound product through an ester linkage. If the holder is a copolymer containing maleic anhydride, it is directly reacted with the hapten to form a hapten-holder bound product through an ester linkage.

Typical examples of the hapten-holder bound product are given below.

Polyacrylic acid combined with 17-amino-1,3,5(10)-estratrien-3-ol, methyl vinyl ether/maleic anhydride copolymer combined with 17-amino-1,3,5(10)-estratrien-3-ol, polyacrylic acid combined with estriol 16-glucuronide, methyl vinyl ether/maleic anhydride copolymer combined with estriol 16-glucuronide, polyacrylic acid combined with estriol 16, 17-dihemisuccinate, polyacrylic acid combined with pregnanediol 3-glucuronide, methyl vinyl ether/maleic anhydride copolymer combined with pregnanediol 3-glucuronide, polyacrylic acid combined with pregnanetriol 3-glucuronide, methyl vinyl ether/maleic anhydride copolymer combined with pregnanetriol 3-glucuronide, polyacrylic acid combined with $3\alpha,11\beta,17\alpha,21$ tetrahydroxypregnan-20-one 3-glucuronide, methyl vinyl ether/maleic anhydride copolymer combined with $3\alpha,11\beta,17\alpha,21$-tetrahydroxypregnan-20-one glucuronide, polyacrylic acid combined with carboxymethylmorphine, methyl vinyl ether/maleic anhydride copolymer combined with carboxymethylmorphine, polyacrylic acid combined with etiocholanolone hemisuccinate, methyl vinyl ether/maleic anhydride copolymer combined with thyroxine, polyacrylic acid combined with thyroxine, polyacrylic acid combined with methanephrine, methyl vinyl ether/maleic anhydride copolymer combined with methanephrine, Reactive Polymeric Latex If desired, the holder may further be chemically combined with a reactive polymeric latex. The polymeric latex has an average particle diameter of about 0.01 to about 2 microns and contains a functional group capable of reacting with the holder. Those having an average particle diameter of about 0.05 to about 1.5 microns are especially suitable.

As such reactive polymeric latices, various polymeric latices composed of a substrate polymer such as polystyrene, a styrene/butadiene copolymer, a styrene/divinylbenzene copolymer, a styrene/divinylbenzene copolymer, polyvinyl toluene and a vinyltoluene/tertiary butyl styrene copolymer and having a functional group such as a carboxyl group, a primary amino group or a carbamide group ($-CONH_2$) are commercially supplied under various tradenames. All of these polymeric latices can be used in this invention. The substrate of the polymeric latices, however, is not limited to these exemplified polymers or copolymers.

When the polymeric latex contains a primary amino group as a functional group, it is directly reacted with the carboxyl group of the holder to bind the holder chemically to the polymeric latex through an amide linkage. Formation of such an amide linkage can be effected by using the reaction procedures already described hereinabove with regard to the reaction between the hapten (or its modified product) and the holder.

When both of the polymeric latex and the holder contain a carboxyl group as a functional group, it is possible to modify the carboxyl group of the latex chemically by the following method to introduce a primary amino group and then bind the latex to the holder through an amide linkage. For example, this can be achieved by a method which comprises reacting the carboxyl-containing latex with a polymethylenediamine such as heptamethylenediamine in the presence of a water-soluble carbodiimide to introduce a primary amino group (for example, Journal of Cell Biology, Vol. 64, pages 75-88, 1975).

Alternatively, an alkylenediamine derivative in which one amino group is protected, such as N-$\epsilon$-tert-butoxycarbonyl lysine methyl ester or N-phthaloyl-N'-methyltrimethylenediamine may be reacted with a latex having a carboxyl group. The reaction can be carried out by using a method selected from those employed for the formation of an amide linkage to bind the hapten to the holder. It is necessary, however, that the reaction be carried out so as not to change the physical properties, such as the particle diameter, of the latex. For this purpose, it is desirable to carry out the reaction in a system containing water. A carbodiimide method to be effected in water using a water-soluble carbodiimide is especially preferred. Elimination of the amino protecting group after the reaction gives a reactive polymeric latex having an amino group as a reactive group. By reacting the resulting reactive polymeric latex with the holder combined with the hapten or its modified product containing a carboxyl group in accordance with the method of forming an amide linkage as described hereinabove, the assay reagent of this invention can be obtained. When the use of N-ε-tert-butoxycarbonyl lysine methyl ester is taken up as an example, the aforesaid reaction is expressed by the following scheme.

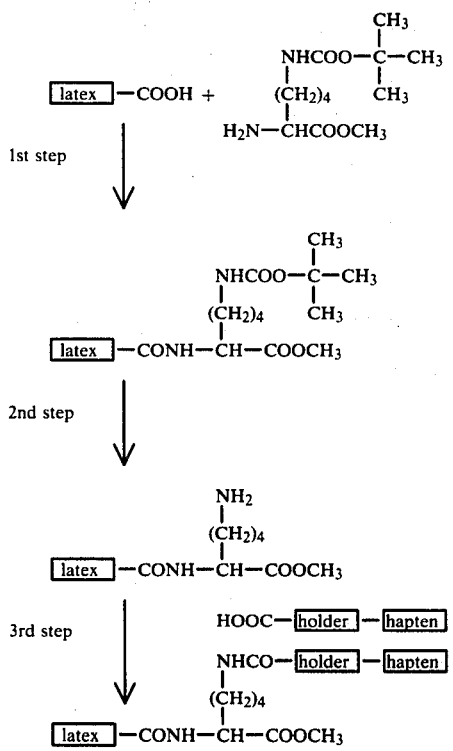

The reaction in the third step can be carried out in quite the same way as in the reaction in the first step.

A similar assay reagent can be obtained also by reversing the sequence of reactions as shown below.

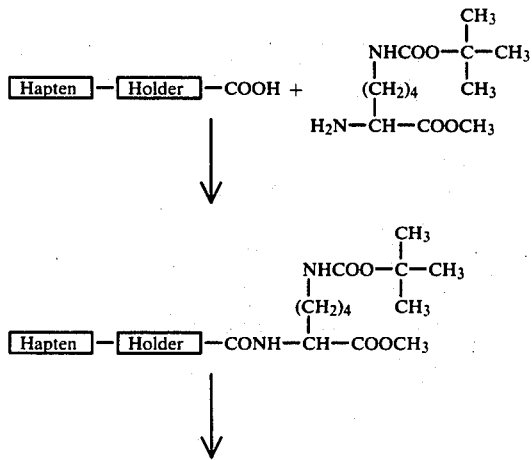

-continued

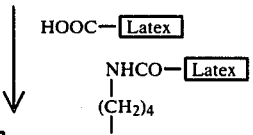

Thus, by combining the hapten-holder bound product with the reactive latex by a chemical reaction, a hapten-holder-latex bound product can be produced.

Specific examples of the hapten-holder-latex bound product are shown below.

Latex linked to (polyacrylic acid combined with estriol 16-glucuronide), latex linked to (polyacrylic acid combined with estriol 16,17-dihemisuccinate), latex linked to (polyacrylic acid combined with 17-amino-1,3,5(10)-estratrien-3-ol), latex linked to (methyl vinyl ether/maleic anhydride copolymer combined with 17-amino-1,3,5(10)-estratrien-3-ol), latex linked to (methyl vinyl ether/maleic anhydride copolymer combined with estriol 16-glucuronide), latex linked to (methyl vinyl ether/maleic anhydride copolymer combined with estriol 16,17-dihemisuccinate), latex linked to (polyacrylic acid combined with pregnanediol 3-glucuronide), latex linked to (methyl vinyl ether/maleic anhydride copolymer combined with pregnanediol 3-glucuronide), latex linked to (polacrylic acid combined with 3α,11β,17α,21-tetrahydroxypregnan-20-one 3-glucuronide), latex linked to (methyl vinyl ether/maleic anhydride copolymer combined with 3α,11β,17α,21-tetrahydroxypregnan-20-one 3-glucuronide), latex linked to (polyacrylic acid combined with carboxymethylmorphine), latex linked to (methyl vinyl ether/maleic anhydride copolymer combined with carboxymethylmorphine), latex linked to (polyacrylic acid combined with etiocholanolone succinate), latex linked to (polyacrylic acid combined with thyroxine), latex linked to (methyl vinyl ether/maleic anhydride copolymer combined with thyroxine, latex linked to (polyacrylic acid combined with metanephrine), latex linked to (methyl vinyl ether/maleic anhydride copolymer combined with metanephrine).

Preparation of Antibodies

The hapten antibody used in this invention can be produced by known methods.

Since the hapten itself does not have antigenicity, it is combined with a substance having antigenicity. The bound product is used as an antigen and an animal is immunized with it to form an antiserum.

The hapten used for this purpose may be any of those haptens or chemically modified products thereof described hereinabove. The hapten is combined with an antigenic substance such as bovine serum albumin, rabbit serum albumin, human serum albumin, bovine gamma-globulin, rabbit gamma-globulin, human gamma-globulin, tetanus toxin, and pneumonococcus polysaccharide, and for example, a hapten-protein bound product may be applied to an animal for immunization.

Examples of the hapten-protein bound product used at this time are steroid-protein bound products such as estriol-16,17-dihemisuccinate-BSA (bovine serum albumin), estriol 16-glucuronide-BSA, 6-oxo-estriol 6-(o-carboxymethyl)oxime-BSA, dehydroepiandrosterone glucuronide-BSA, androsterone hemisuccinate-BSA, and cortisol 21-hemisuccinate-BSA, and products obtained by binding haptens other than the steroids to antigenic substances such as proteins. In immunizing an animal with such a bound product, the joint use of adjuvants such as complete Freund's adjuvant permits more effective production of an antiserum.

Animals that can be used for this purpose are mammals such as rabbits, goats, sheep, and guinea pigs. The resulting antiserum is caused to be absorbed by the substance having antigenicity used for bonding to the hapten, and gamma-globulin is separated by such means as alcohol precipitation or salting out. Thus, a hapten antibody can be obtained. Hapten antibody-supported carriers.

The carrier, as referred to in this invention, denotes any carrier which can be used conventionally in immunochemical assay reagents, and includes, for example, erythrocytes of humans, sheep, rabbits, etc., latices, bentonite, collodion, cholesterol crystals, silica, and kaolin. Any materials which can carry the hapten antibody may be used in the present invention.

Sensitization of the carrier with the hapten antibody, as referred to in the present invention, means the adsorption of the antibody to the carrier, and does not means the chemical bonding of the antibody to the carrier. Accordingly, when the antibody is combined chemically with a synthetic resin, etc., the product is referred to as a polymeric latex having the antibody chemically combined therewith. These two types of carriers are inclusively referred to in this invention as hapten antibody-supported carriers.

Polymeric Latices Sensitized or Chemically Combined with Antibodies

In the present invention, the antibody obtained in the aforesaid manner is chemically combined with a polymeric latex, etc. or the latex is sensitized with the antibody. Such a latex may or may not contain functional groups of the types exemplified hereinabove. However, when the antibody is to be chemically combined with the latex, it is necessary to use polymeric latices which have functional groups capable of reacting with such antibody. Such polymeric latices have an average particle diameter of about 0.01 to about 2 microns, and contain functional groups capable of reacting with the antibodies. Those having an average particle diameter of about 0.05 to about 1.5 microns are especially suitable.

Polymeric latices composed of a substrate such as polystyrene, a styrene/butadiene copolymer, a styrene/divinylbenzene copolymer, polyvinyltoluene, and a vinyltoluene/tert.-butylstyrene and having such a functional group as a carboxyl group, a primary amino group or a carbamide group ($-CONH_2$) are commercially supplied under various tradenames as such reactive latices. The substrate of the latices is not limited to these exemplified polymers or copolymers.

When the polymeric latex contains a carboxyl group or a primary amino group as a functional group, it may be directly reacted with the amino group or carboxyl group of the antibody to bind it chemically to the antibody through an amide linkage. Such an amide linkage can be formed by any of the aforesaid methods for chemically binding the hapten or its chemically modified product to the holder.

When both of the latex and the antibody have a carboxyl group as a functional group, it is possible to modify the carboxyl group of either one of them chemically by the aforesaid method to introduce a primary amino group, and to bind the latex to the antibody through an amide linkage. For example, there is available a method which comprises reacting the latex containing a carboxyl group with a polymethylenediamine such as heptamethylenediamine in the presence of a water-soluble carbodiimide to introduce a primary amino group (for example, Journal of Cell Biology, Vol. 64, pages 75–88, 1975).

However, since antibodies have both a carboxyl group and a primary amino group in many cases, it is usually possible to chemically bind them to each other by such a means as the carbodiimide method without the need for performing the aforesaid chemical modification. Specifically, for example, by binding an anti-estriol 16-glucuronide antibody to a carboxyl-containing latex by the carbodiimide method, an anti-estriol 16-glucuronide antibody-linked latex can be obtained.

Examples of the hapten antibody-linked latex are given below.

Latex combined with anti-estriol 16-glucuronide antibody, latex combined with anti-estriol 16,17-dihemisuccinate antibody, latex combined with anti-17-amino-1,3,5(10)-estratrien-3-ol antibody, latex combined with anti-pregnanediol 3-glucuronide antibody, latex combined with anti-pregnanetriol 3-glucuronide antibody, latex combined with anti-3,11,17,21-tetrahydroxy-pregnan-20-one 3-glucuronide antibody, latex combined with anti-carboxymethylmorphine, latex combined with anti-etiocholanolone hemisuccinate antibody, latex combined with anti-thyroxine antibody, latex combined with anti-metanephrine antibody.

The latex combined with the anti-heptan antibody in accordance with this invention, however, is not limited to the above specific examples.

As stated hereinabove, sensitization of the carrier with the hapten antibody means the adsorption of the antibody to the carrier. An antibody-sensitized carrier can be obtained by merely mixing a solution of the antibody with a suspension of the carrier with stirring.

For example, erythrocytes as a carrier can be sensitized with the hapten antibody by an ordinary method of producing antibody-sensitized erythrocytes. For example, the red cells are fixed with a suitable material such as formalin, glutaraldehyde or pyruvaldehyde, and then sensitized with the antibody optionally using tannic acid or other condensing agents to form antibody-sensitized cells. These are used as a suspension, or if required, they are lyophilized to form antibody-sensitized erythrocytes (antibody-sensitized carrier).

A polymeric latex as a carrier may be sensitized with the antibody in the same way as in the conventional method to produce an antibody-sensitized latex. For example, by adding a suspension of a such a carrier as a polystyrene latex to a solution of the antibody in a suitable concentration and mixing them, an antibody-sensitized latex can be obtained.

Examples of the hapten antibody-sensitized carrier are given below.

Erythrocytes sensitized with anti-estriol-16-glucuronide antibody, erythrocytes sensitized with anti-estriol-16,17-dihemisuccinate, erythrocytes sensitized with anti-17-amino-1,3,5(10)-estratrien-3-ol antibody, erythrocytes sensitized with anti-pregnanediol 3-glucuronide antibody, erythrocytes sensitized with anti-pregnanetriol 3-glucuronide antibody, erythrocytes sensitized with anti-3α,11β,17α,21-tetrahydroxypregnan-20-one 3-glucuronide antibody, erythrocytes sensitized with anti-carboxymethylmorphine, erythrocytes sensitized with anti-etiocholanolone hemisuccinate antibody, erythrocytes sensitized with anti-throxine antibody, erythrocytes sensitized with anti-metanephrine antibody, latex sensitized with anti-estriol 16-glucuronide antibody, latex sensitized with anti-estriol 16,17-dihemisuccinate antibody, latex sensitized with anti-17-amino-1,3,5(10)-estratrien-3-ol antibody, latex sensitized with anti-pregnanediol 3-glucuronide antibody, latex sensitized with anti-pregnanetriol 3-glucuronide antibody, latex sensitized with anti-3α,11β,17α,21-tetrahydroxypregnan-20-one 3-glucuronide antibody, latex sensitized with anti-carboxymethylmorphine antibody, latex sensitized with anti-etiocholanolone hemisuccinate antibody, latex sensitized with anti-thyroxine antibody, and latex sensitized with anti-metanephrine antibody.

The hapten antibody-sensitized carrier in accordance with this invention, however, are not limited to these specific examples.

The present invention made up of the above described constituent elements thus provides a novel immunochemical assay reagent comprising a combination of (1) a carboxyl-containing water-soluble monoolefinic polymeric compound combined with a hapten or its chemically modified product, or a latex linked to the carboxyl-containing water-soluble mono-olefinic polymeric compound combined with hapten, and (2) a hapten antibody (or in dilution), or a hapten antibody-supported carrier such as a carrier sensitized with the hapten antibody by adsorption of a hapten antibody to a carrier, or a carrier chemically combined with the hapten antibody such as a latex chemically combined with the hapten antibody, and an immunochemical assay method characterized by using the aforesaid reagent.

Specific examples of the novel immunochemical assay reagent of this invention are given below.

1. Immunochemical assay reagents for the determination of estrogen consisting of A and B:

(a)

A: latex linked to (polyacrylic acid combined with estriol 16-glucuronide) and

B: latex combined with anti-estriol 16-glucuronide antibody (b)

A: latex linked to (polyacrylic acid combined with estriol 16,17-dihemisuccinate) and B: latex combined with anti-estriol 16,17-dihemisuccinate antibody (c)

A: latex linked to (methyl vinyl ether/maleic anhydride copolymer combined with estriol 16-glucuronide) and B: latex combined with anti-estriol antibody (d)

A: latex linked to (methyl vinyl ether/maleic anhydride copolymer combined with estriol 16,17-dihemisuccinate) and B: latex combined with anti-estriol antibody (e)

A: latex linked to (polyacrylic acid combined with estriol 16-glucuronide) and

B: latex sensitized with anti-estriol 16-glucuronide antibody (f)

A: latex linked to (polyacrylic acid combined with estriol 16,17-dihemisuccinate) and B: latex sensitized with anti-estriol 16,17-disuccinate antibody combined (g)

A: latex linked to (polyacrylic acid combined with estriol 16-glucuronide) and

B: anti-estriol 16-glucuronide antibody (h)

A: latex linked to (polyacrylic acid combined with 17-amino-1,3,5(10)-estratrien-3-ol) and B: latex combined with anti-estriol 16-glucuronide antibody (i)

A: polyacrylic acid combined with estriol 16-glucuronide and

B: latex combined with anti-estriol 16-glucuronide antibody (j)

A: polyacrylic acid combined with estriol 16,17-dihemisuccinate and

B: latex combined with anti-estriol 16,17-dihemisuccinate antibody (k)

A: methyl vinyl ether/maleic anhydride copolymer combined with estriol 16-glucuronide and B: latex combined with anti-estriol antibody (l)

A: methyl vinyl ether/maleic anhydride copolymer combined with estriol 16,17-dihemisuccinate and B: latex combined with anti-estriol antibody (m)

A: polyacrylic acid combined with estriol 16-glucuronide and

B: latex sensitized with anti-estriol 16-glucuronide antibody or erythrocytes sensitized with anti-estriol 16-glucuronide antibody (n)

A: polyacrylic acid combined with estriol 16,17-dihemisuccinate and

B: latex combined with anti-estriol 16,17-dihemisuccinate antibody or erythrocytes sensitized with anti-estriol 16,17-dihemisuccinate antibody (o)

A: polyacrylic acid combined with 17-amino-1,3,5(10)-estratrien-3-ol and

B: latex combined with anti-estriol 16-glucuronide antibody

2. Immunochemical assay reagents for the determination of pregnandiol consisting of A and B:

(a)

A: latex linked to (polyacrylic acid combined with pregnanediol 3-glucuronide) and B: latex combined with anti-pregnanediol 3-glucuronide antibody (b)

A: latex linked to (methyl vinyl ether/maleic anhydride copolymer combined with pregnanediol 3-glucuronide) and B: latex combined with anti-pregnanediol 3-glucuronide antibody (c)

A: latex linked to (polyacrylic acid combined with pregnanediol 3-glucuronide) and B: latex sensitized with anti-pregnanediol 3-glucuronide antibody (d)

A: latex linked to (polyacrylic acid combined with pregnanediol 3-glucuronide) and B: anti-pregnanediol 3-glucuronide antibody (e)

A: latex linked to (methyl vinyl ether/maleic anhydride copolymer combined with pregnanediol 3-glucuronide) and B: anti-pregnanediol 3-glucuronide antibody (f)

A: polyacrylic acid combined with pregnanediol 3-glucuronide and

B: latex combined with anti-pregnanediol 3-glucuronide antibody (g)

A: methyl vinyl ether/maleic anhydride copolymer combined with pregnanediol 3-glucuronide and B: latex combined with anti-pregnanediol 3-glucuronide antibody (h)

A: polyacrylic acid combined with pregnanediol 3-glucuronide

B: latex sensitized with anti-pregnanediol 3-glucuronide antibody (i)

A: polyacrylic acid combined with pregnanetriol 3-glucuronide and

B: latex combined with anti-pregnanetriol 3-glucuronide antibody (j)

A: methyl vinyl ether/maleic anhydride copolymer combined with pregnanediol 3-glucuronide and B: latex combined with anti-pregnanediol 3-glucuronide antibody 3. Immunochemical assay reagents for the determination of 17-OHCS consisting of A and B:

(a)

A: latex linked to (polyacrylic acid combined with $3\alpha,11\beta,17\alpha,21$-tetrahydroxypregnan-20-one 3-glucuronide) and B: latex combined with anti-$3\alpha,11\beta,17\alpha,21$-tetrahydroxypregnan-2-one 3-glucuronide antibody (b)

A: latex linked to (methyl vinyl ether/maleic anhydride copolymer combined with $3\alpha,11\beta,17\alpha,21$-tetrahydroxypregnan-20-one 3-glucuronide) and B: latex combined with anti-$3\alpha,11\beta,17\alpha,21$-tetrahydroxypregnan-20-one 3-glucuronide antibody (c)

A: latex linked to (polyacrylic acid combined with $3\alpha,11\beta,17\alpha,21$-tetrahydroxypregnan-20-one 3-glucuronide) and B: latex sensitized with anti-$3\alpha,11\beta,17\alpha,21$-tetrahydroxypregnan-20-one 3-glucuronide antibody (d)

A: latex linked to (polyacrylic acid combined with $3\alpha,11\beta,17\alpha,21$-tetrahydroxypregnan-20-one 3-glucuronide) and B: anti-$3\alpha,11\beta,17\alpha,21$-tetrahydroxypregnan-20-one 3-glucuronide antibody (e)

A: latex linked to (methyl vinyl ether/maleic anhydride copolymer combined with $3\alpha,11\beta,17\alpha,21$-tetrahydroxypregnan-20-one 3-glucuronide) and B: latex sensitized with anti-$3\alpha,11\beta,17\alpha,21$-tetrahydroxypregnan-20-one antibody (f)

A: latex linked to (methyl vinyl ether/maleic anhydride copolymer combined with $3\alpha,11\beta,17\alpha,21$-tetrahydroxypregnan-20-one 3-glucuronide) and B: anti-$3\alpha,11\beta,17\alpha,21$-tetrahydroxypregnan-20-one 3-glucuronide antibody (g)

A: polyacrylic acid combined with $3\alpha,11\beta,17\alpha,21$-tetrahydroxypregnan-20-one 3-glucuronide and B: latex combined with anti-$3\alpha,11\beta,17\alpha,21$-tetrahydroxypregnan-20-one 3-glucuronide antibody (h)

A: methyl vinyl ether/maleic anhydride copolymer combined with 3α,11β,17α,21-tetrahydroxypregnan-20-one glucuronide and B: latex combined with anti-3α,11β,17α,21-tetrahydroxypregnan-20-one 3-glucuronide antibody (i)

A: polyacrylic acid combined with 3α,11β,17α,21-tetrahydroxypregnan-20-one 3-glucuronide and B: latex sensitized with anti-3α,11β,17α,21-tetrahydroxypregnan-20-one 3-glucuronide antibody (j)

A: polyacrylic acid combined with 3α,11β,17α,21-tetrahydroxypregnan-20-one 3-glucuronide and B: erythrocytes sensitized with anti-3α,11β,17α,21-tetrahydroxypregnan-20-one 3-glucuronide antibody (k)

A: methyl vinyl ether/maleic anhydride copolymer combined with 3α,11β,17α,21-tetrahydroxypregnan-20-one 3-glucuronide and B: erythrocytes sensitized with anti-3α,11β,17α,21-tetrahydroxypregnan-20-one glucuronide antibody 4. Immunochemical assay reagents for the determination of morphine consisting of A and B:

(a)

A: latex linked to (polyacrylic acid combined with carboxymethylmorphine)

B: latex combined with anti-carboxymethylmorphine antibody (b)

A: latex linked to (methyl vinyl ether/maleic anhydride copolymer combined with carboxymethylmorphine) and B: latex combined with anti-carboxymethylmorphine antibody (c)

A: latex linked to (polyarcylic acid combined with carboxymethylmorphine) and

B: latex sensitized with anti-carboxymethylmorphine antibody (d)

A: latex linked to (methyl vinyl ether/maleic anhydride copolymer combined with carboxymethylmorphine) and B: latex sensitized with anti-carboxymethylmorphine antibody (e)

A: latex linked to (polyacrylic acid combined with carboxymethylmorphine) and

B: anti-carboxymethylmorphine antibody (f)

A: latex linked to (methyl vinyl ether/maleic anhydride copolymer combined with carboxymethylmorphine) and B: anti-carboxymethylmorphine antibody (g)

A: polyacrylic acid combined with carboxymethylmorphine

B: latex combined with anti-carboxymethylmorphine antibody (h)

A: methyl vinyl ether/maleic anhydride copolymer combined with carboxymethylmorphine and B: latex combined with anti-carboxymethylmorphine antibody (i)

A: polyacrylic acid combined with carboxymethylmorphine and

B: erythrocytes sensitized with anti-carboxymethylmorphine antibody (j)

A: methyl vinyl ether/maleic anhydride copolymer combined with carboxymethylmorphine and B: erythrocytes sensitized with anti-carboxymethylmorphine antibody (k)

A: polyacrylic acid combined with carboxymethylmorphine and

B: latex sensitized with anti-carboxymethylmorphine antibody (l)

A: methyl vinyl ether/maleic anhydride copolymer combined with carboxymethylmorphine and B: latex sensitized with anti-carboxymethylmorphine antibody 5. Immunochemical assay reagents for the determination of 17-KS consisting of A and B:

(a)

A: latex linked to (polyacrylic acid combined with etiocholanolone hemisuccinate) and B: latex combined with anti-etiocholanolone hemisuccinate antibody (b)

A: latex linked to (methyl vinyl ether/maleic anhydride copolymer combined with etiocholanolone hemisuccinate) and B: latex combined with anti-etiocholanolone hemisuccinate antibody (c)

A: latex linked to (polyacrylic acid combined with etiocholanolone hemisuccinate) and B: latex sensitized with anti-etiocholanolone hemisuccinate antibody (d)

A: latex linked to (methyl vinyl ether/maleic anhydride copolymer combined with etiocholanolone hemisuccinate) and B: latex sensitized with anti-etiocholanolone hemisuccinate antibody (e)

A: latex linked to (polyacrylic acid combined with etiocholanolone hemisuccinate) and B: anti-etiocholanolone hemisuccinate antibody (f)

A: latex linked to (methyl vinyl ether/maleic anhydride copolymer combined with etiocholanolone hemisuccinate) and
B: anti-etiocholanolone hemisuccinate antibody (g)

A: polyacrylic acid combined with etiocholanolone hemisuccinate and
B: latex combined with anti-etiocholanolone hemisuccinate antibody (h)

A: methyl vinyl ether/maleic anhydride copolymer combined with etiocholanolone hemisuccinate and
B: latex combined with anti-etiocholanolone hemisuccinate antibody (i)

A: polyacrylic acid combined with etiocholanolone hemisuccinate and
B: latex sensitized with anti-etiocholanolone hemisuccinate antibody (j)

A: methyl vinyl ether/maleic anhydride copolymer combined with etiocholanolone hemisuccinate and
B: latex sensitized anti-etiocholanolone antibody (k)

A: acrylic acid combined with etiocholanolone hemisuccinate and
B: erythrocytes sensitized with anti-etiocholanolone hemisuccinate antibody (l)

A: methyl vinyl ether/maleic anhydride copolymer combined with etiocholanolone hemisuccinate and
B: erythrocytes sensitized with anti-etiocholanolone antibody 6. Immunochemical assay reagents for the determination of thyroxine ($T_4$) consisting of A and B:

(a)

A: latex linked to (polyacrylic acid combined with thyroxine) and
B: latex combined with anti-thyroxine antibody (b)

A: latex linked to (methyl vinyl ether/maleic anhydride copolymer combined with thyroxine) and
B: latex combined with anti-thyroxine antibody (c)

A: latex linked to (polyacrylic acid combined with thyroxine) and
B: latex combined with anti-thyroxine antibody (d)

A: latex linked to (methyl vinyl ether and maleic anhydride combined with thyroxine) and
B: latex sensitized with anti-thyroxine antibody (e)

A: latex linked to (polyacrylic acid combined with thyroxine) and
B: anti-thyroxine antibody (f)

A: latex linked to (methyl vinyl ether/maleic anhydride copolymer combined with thyroxine) and
B: anti-thyroxine antibody (g)

A: polyacrylic acid combined with thyroxine and
B: latex combined with anti-thyroxine antibody (h)

A: methyl vinyl ether/maleic anhydride copolymer combined with thyroxine and
B: latex combined with anti-thyroxine antibody (i)

A: polyacrylic acid combined with thyroxine and
B: latex sensitized with anti-thyroxine antibody (j)

A: methyl vinyl ether/maleic anhydride copolymer combined with thyroxine and
B: latex sensitized with anti-thyroxine antibody (k)

A: polyacrylic acid combined with thyroxine and
B: erythrocytes sensitized with anti-thyroxine antibody (l)

A: methyl vinyl ether/maleic anhydride copolymer combined with thyroxine
B: erythrocytes sensitized with anti-thyroxine antibody 7. Immunochemical assay reagents for the determination of catecholamine consisting of A and B:

(a)

A: latex linked to (polyacrylic acid combined with metanephrine) and
B: latex combined with anti-metanephrine antibody (b)

A: latex linked to (methyl vinyl ether/maleic anhydride copolymer combined with metanephrine) and
B: latex combined with anti-metanephrine antibody (c)

A: latex linked to (polyacrylic acid combined with metanephrine) and
B: latex combined with anti-metanephrine antibody (d)

A: latex linked to (methyl vinyl ether/maleic anhydride copolymer combined with metanephrine) and
B: latex sensitized with anti-metanephrine antibody (e)

A: latex linked to (polyacrylic acid combined with metanephrine) and
B: anti-metanephrine antibody (f)

A: latex linked to (methyl vinyl ether/maleic anhydride copolymer combined with metanephrine) and
B: anti-metanephrine antibody (g)

A: polyacrylic acid combined with metanephrine and
B: latex combined with anti-metanephrine antibody (h)

A: methyl vinyl ether/maleic anhydride copolymer combined with metanephrine and
B: latex combined with anti-metanephrine antibody (i)

A: polyacrylic acid combined with metanephrine and
B: latex sensitized with anti-metanephrine antibody (j)

A: methyl vinyl ether/maleic anhydride copolymer combined with metanephrine and
B: latex sensitized with anti-metanephrine antibody (k)

A: polyacrylic acid combined with metanephrine and
B: erythrocytes sensitized with anti-metanephrine antibody (l)

A: methyl vinyl ether/maleic anhydride copolymer combined with metanephrine and
B: erythrocytes sensitized with anti-metanephrine antibody.

The reagents in accordance with this invention, however, are not limited to these specific examples.

In the examples 1 to 7 above, polyacrylic acid is mainly given as the holder of the hapten-bound holder in A. If desired, it can be replaced, for example, by a methyl vinyl ether/maleic anhydride copolymer, and in these examples, antibody-sensitized erythrocytes can be used instead of the antibody-sensitized latices.

Immunochemical assay using the novel reagent of this invention can be performed in the following manner.

Immunochemical Assay Method

Traces of haptens existing in urine, blood or other body fluids can be easily and rapidly determined by using the reagents of this invention. The theory of determination is based on an agglutination inhibiting reaction in which a hapten to be determined inhibits an agglutination reaction between the hapten-bound carboxyl-containing mono-olefinic polymeric compound or the latex combined with the hapten-bound carboxyl-containing mono-olefinic polymeric compound and the hapten antibody or the hapten antibody-sensitized (or chemically bound) carrier, especially a hapten antibody-bound latex.

Specific procedures of determination are shown in Examples to be given hereinbelow. General methods of determination are as follows:

(1) One drop of an assay sample (optionally diluted) is placed on a clean slide, and then one drop of a suspension of the aforesaid hapten antibody or the hapten antibody-sensitized (or chemically bound) latex is put onto the assay sample. The two are fully mixed, and then one drop of a solution of the hapten-bound carboxyl-containing mono-olefinic polymeric compound or a suspension of the latex combined with the hapten-bound polymeric compound is put into the mixture. The slide is rocked for 2 minutes, and observed with the naked eye. The presence of an agglutinated pattern is judged to be "negative", and the presence of an agglutination inhibited pattern (non-agglutinated pattern), "positive".

The hapten concentration in the assay sample can be determined by performing the test after optionally diluting the assay sample, and multiplying the maximum ratio of dilution at which a positive pattern appears by the assay sensitivity.

The assay method in accordance with this invention is not limited to the above one. For example, it is possible to dissolve a predetermined amount of the hapten-bound product in a liquid for diluting the assay sample, and react the diluted assay sample with the antibody-sensitized (or chemically bound) latex.

(2) 0.1 ml of an assay sample (optionally diluted) is put into a clean round-bottomed test tube, and 0.3 ml of hapten antibody-sensitized erythrocytes are added. They are fully stirred, and then 0.1 ml of a solution of the hapten-bound carboxyl-containing water-soluble mono-olefinic polymeric compound is added. After stirring, the test tube is allowed to stand for 2 hours on a stand equipped with a mirror. Then, the hapten is determined by a pattern formed at the bottom of the test tube. At this time, the agglutination inhibited pattern forms a sedimentation ring, and the agglutinated pattern looks like a mat.

The method of this invention is not limited to these embodiments. For example, it is also possible to dissolve a predetermined amount of the aforesaid hapten-bound product in a liquid for diluting the assay sample, and react predetermined amount of the diluted assay sample with the hapten antibody-sensitized erythrocytes.

Characteristic Features and Advantages of the Invention

The characteristic feature of the reagent of this invention is a combination of (A) a carboxyl-containing water-soluble mono-olefinic polymeric compound combined with a hapten or its chemically modified product (to be sometimes referred to hereinbelow as component A-1), or a hapten-supported latex (to be sometimes referred to hereinbelow as component A-2) resulting from the chemically binding of the component A-1 to a polymeric latex having a particle diameter of about 0.01 to about 2 microns, and (B) a hapten antibody (to be sometimes referred to hereinbelow as component B-1), or a hapten antibody-supported carrier (to be sometimes referred to hereinbelow as component B-2) comprising a carrier sensitized or chemically bound with the hapten antibody.

When the component A-1 is used as the component (A), it must be used in combination with the component B-2.

Thus, examples of the combination of component A with component B in this invention are as follows:

(1) a combination of component A-1 with component B-2, (2) a combination of component A-2 with component B-1, (3) a combination of component A-2 with component B-2.

Of these, the combinations (2) and (3) are preferred, and the combination (3) is especially preferred.

In the method of determining haptens by an immunological latex agglutination inhibiting reaction, it has been the usual practice to use an agglutination reaction system involving a hapten antibody and an antigen-sensitized latex obtained by sensitizing a polymeric latex with an antigen resulting from the binding of a hapten to a strongly antigenic substance such as bovine serum albumin, human serum albumin, bovine gamma-globulin or tetanus toxin, and an agglutination reaction system involving a hapten antibody-sensitized latex and the aforesaid strongly antigenic substance having a hapten bound thereto. It has now been found by the present invention that the various characteristics and advantages described below can be obtained by using the carboxyl-containing water-soluble mono-olefinic polymeric compound which is different from the conventionally used natural products having strong antigenicity such as proteins or analogs thereof, chemically binding a hapten to such a polymeric compound (to form component A-1), or further binding the component A-1 chemically to a polymeric latex (to form component A-2).

The components A-1 and A-2 show very high stability in the form of an aqueous solution or aqueous suspension and can fully withstand storage at room temperature.

In the conventional reagents of this type, the aforesaid natural products or analogs thereof are used for combination with haptens, and therefore in long-term storage, these substances combined with haptens are not stable because of denaturation or decomposition. Hence, the hapten-bound products which have been used so far are unstable in the form of solution, and cannot be stored even for a short period of time and in a cold place. For this reason, they have to be stored only after lyophilization. Also, if the latex sensitized with hapten-bound holder is lyophilized, the properties of the latex itself will be changed and may cause a nonspecific agglutination reaction. Thus, in practice, it cannot be lyophilized, and has to rely on storage in a cold place.

In contrast, the components A-1 and A-2 used in this invention are very stable because they are prepared from carboxyl-containing water-soluble mono-olefinic polymeric compounds which are quite irrelevant to the constituents of animals.

When the carboxyl-containing mono-olefinic polymeric compound combined with a hapten is linked to a polymeric latex (component A-2), the product (component A-2) has very high stability because of strong chemical binding to the polymeric latex different from the conventional sensitization.

The method of this invention can achieve the desired assay in a shorter reaction time than the conventional assay methods, and has a higher assay sensitivity. The conventional methods require a reaction time of 3 to 5 minutes, and when the amount of the reaction liquid is small or when the reaction time for assay reaches nearly 5 minutes owing to the environmental conditions (e.g., temperature, humidity, etc.) of a room where the determination is made, the reagent is apt to be dried, and a nonspecific reaction pattern tends to form from its periphery. According to the method of this invention, determination can be easily made in 2 to 3 minutes in the agglutination reaction systems (1) and (2) described above. In particular, in the agglutination reaction system (3), determination can be made easily in 1 to 2 minutes.

By a latex agglutination inhibiting reaction, haptens can be determined by the inhibited pattern, as stated hereinabove, but the intensity of the agglutination pattern constitutes a factor for determining the ease of viewing and judgement. According to this invention, an agglutinated pattern appears far earlier than in the conventional methods, and moreover, the agglutinated pattern can be clearly distinguished from an agglutination inhibited pattern. This is presumably because the reactivity of the reagent with an antibody is increased by the use of the carboxyl-containing water-soluble mono-olefinic polymeric compound as a holder unlike the conventional methods in which natural products or the analogs thereof are used. With the agglutination system (3) described hereinabove, the aforesaid effect can be expected to increase because the antibody is bound to a latex and the antibody-bound latex directly participates in the agglutination reaction. In the conventional agglutination reaction, the antigen-sensitized latex reacts with diluted antiserum, and the antibody which has reacted with the antigen of the antigen-sensitized latex further reacts with the antigen-sensitized latex. Thus, the agglutination of the antigen-sensitized latex gradually grows and finally forms an agglutinated pattern that can be viewed with the naked eye. In contrast, in the agglutination system (3) in accordance with this invention, the antibody is also bound to the latex, and therefore an antigen-antibody reaction between the hapten bound to the surface of the latex through the holder and the antibody supported on the latex directly participates in agglutination. The agglutination of the hapten and antibody through the latex grows, and an agglutinated pattern forms earlier and more strongly. Moreover, the agglutination inhibiting action can be discerned clearly and rapidly.

The carboxyl-containing water-soluble monoolefinic polymeric compound (holder), and the component A-1 obtained by chemically binding a hapten or its chemically modified product to the holder do not substantially have antigenicity and are immunologically inactive, as shown in Referential Examples given hereinbelow. It is believed therefore that the component A-2 which is obtained by chemically binding the hapten-bound holder (component A-1) to a polymeric latex neither has substantial antigenicity, and is therefore immunologically inactive.

In the prior art, a protein or its analog having antigenicity is used as a carrier and is sensitized with a hapten. In contrast, in the present invention, by using a product (component A-1) obtained by chemically binding a hapten or its chemically modified product to an immunologically inert holder substantially having no antigenicity, or a product (component A-2) obtained by chemically binding the component A-1 to a polymeric latex, it is possible to obtain an immunochemical assay reagent having very high storage stability and to determine the agglutination reaction of the hapten-bound antibody and the agglutination inhibiting reaction, rapidly, accurately, and with high sensitivity.

In the present invention, the assay sensitivity of the reagent can be adjusted to a level suitable for a subject to be determined by adjusting the amount of the hapten to be bound to the carboxyl-containing water-soluble mono-olefinic polymeric compound, the amount of the hapten-bound carboxyl-containing mono-olefinic polymeric compound to be bound to the latex, and/or the ratio of dilution of the corresponding antiserum or the amount of the antibody to be bound to the polymeric latex; or by changing the concentration of rabbit serum albumin, goat serum albumin, bovine serum albumin, etc. to be added at the time of preparing the final latex; or by using a suitable combination of the above methods.

Table 1 below shows a comparison of the stability of the reagent of this invention with that of a conventional reagent in determining urinary estrogen.

(A) A combination of a solution of polyacrylic acid combined with 17-amino-1,3,5(10)-estratrien-3-ol and a latex sensitized with anti-estriol 16-glucuronide antibody (the reagent of the invention).

(B) A combination of a solution of bovine serum albumine combined with estriol 16-glucuronide and a latex sensitized with anti-estriol 16-glucuronide antibody (conventional reagent).

To compare the stability of (A) with that of (B), the assay sensitivity of each reagent is adjusted to 0.1 μg/ml. The solution of polyacrylic acid combined with 17-amino-1,3,5(10)-estratrien-3-ol in (A), and the bovine serum albumin combined with estriol 16-glucuronide in (B) are stored at 4° C., or at room temperature, and the antibody-sensitized latex is stored at 4° C. The stabilities of these solutions (A) and (B) are compared.

TABLE 1

| Storage temperature | | Assay sensitivity | | | | |
|---|---|---|---|---|---|---|
| | | 1 month | 3 months | 6 months | 12 months | 24 months |
| (A) | 4° C. | 0.1 | 0.1 | 0.1 | 0.1 | 0.1 |
| (B) | 4° C. | 0.1 | 0.1 | 0.08 | 0.05 | — |
| (A) | room temperature | 0.1 | 0.1 | 0.1 | 0.1 | 0.1 |
| (B) | room temperature | 0.1 | 0.05 | — | — | — |

As shown in Table 1, (A) is stable even after storage for 24 months at room temperature, but with (B), the sensitivity increased after storage at 4° C. for 6 to 12 months and after 24 months, no reaction is noted. This tendency is more distinct during storage at room temperature. The sensitivity is doubled after storage for 3 months, and after 6 months, no reaction is noted. In other words, in (B), agglutination with the antibody-sensitized latex becomes weak as the time elapses, and the apparent sensitivity increases. After storage for 24 months at 4° C. and 6 months at room temperature, a reaction which intrinsically should show agglutination does not take place. It is seen from these data that far higher stability can be obtained by binding a hapten to a carboxyl-containing water-soluble mono-olefinic polymeric compound than by binding it to a protein.

Table 2 shows a comparison of the assay sensitivity and the reaction time between the method of this invention and the conventional method in determining urinary estrogen.

TABLE 2

| Method of determination | Assay sensitivity (g/ml) | Reaction time (minutes) |
|---|---|---|
| Method of the invention (A) | $1 \times 10^{-2}$ | 1-2 |
| Method of the invention (B) | $5 \times 10^{-2}$ | 2 |
| Conventional method | $5 \times 10^{-1}$ | 5 |

The method (A) of this invention is performed by using a lysine-latex linked to polyacrylic acid combined with 17-amino-1,3,5(10)-estratrien-3-ol and a latex sensitized with anti-estriol 16-glucuronide antibody. The method (B) of this invention is performed by using a lysine-latex linked to polyacrylic acid combined with 17-amino-1,3,5(10)-estratrien-3-ol and diluted anti-estriol 16-glucuronide antiserum. The conventional method is performed by using a latex sensitized with estriol 16-glucuronide-BSA and diluted anti-estriol 16-glucuronide antiserum. As shown in the table, the methods of this invention has 20 times (in the case of A) and 10 times (in the case of B) as high a sensitivity as the conventional method, and the reaction time can be shortened to 1/25 to 1/5 of that of the conventional method. When an attempt is made in the conventional method to increase the sensitivity further, the agglutinated pattern, which is a negative pattern, becomes weak. It is presumed from this that the high sensitivity in the present invention is due to the increased reactivity of the antigen with an antibody as a result of using the carboxyl-containing water-soluble mono-olefinic polymeric compound. Furthermore, according to the method of this invention, transition from an agglutination inhibited pattern to an agglutinated pattern is more distinct than in the conventional method. Moreover, the margin of concentration in transition is narrower and the method of this invention has a greater assaying ability.

Urinary estrogen which reflects the function of the placenta of a pregnant woman is mainly estriol 16-glucuronide. Standard solutions of estriol 16-glucuronide shown in Table 3 are prepared using glycine-buffered saline solution, and the distinctness of transition from an agglutination inhibited pattern to an agglutinated pattern is determined both in the method of this invention and the conventional method. The results are shown in Table 3. The method (A) of this invention is performed by using a lysine-latex linked to polyacrylic acid combined with estriol 16-glucuronide-lysine and a latex combined with anti-estriol 16-glucuronide antibody. The method (B) of the invention is performed by using the aforesaid linked lysine-latex and diluted anti-estriol 16-glucuronide antiserum. The conventional method is performed by using a latex sensitized with estriol 16-glucuronide-RSA and diluted anti-estriol 16-glucuronide antiserum. In these methods, the sensitivity is adjusted to 0.1 g/ml prior to the testing.

TABLE 3

| Method of determination | Concentration (μg/ml as estriol) of an estriol 16-glucuronide solution | | | | | | |
|---|---|---|---|---|---|---|---|
| | 0.2 | 0.12 | 0.10 | 0.03 | 0.06 | 0.04 | 0 |
| Method (A) of the invention | — | — | — | ++ | +++ | +++ | +++ |
| Method (B) of the invention | — | — | — | + | ++ to +++ | +++ | +++ |
| Conventional method | — | — | — | + | + | + | ++ |

The scale of evaluation is as follows:
—: a complete agglutination inhibited pattern
+: an agglutinated pattern slightly observed visually
++: can be differentiated from an agglutinated pattern with the naked eye
+++: a clear agglutinated pattern In the above table, the formation of an agglutinated pattern is shown by + in order to compare the intensities of the agglutinated patterns.

As shown in the table, in the conventional method, the agglutinated pattern shows a weak intensity even when using only a buffer solution not containing estriol 16-glucuronide, and the margin of concentration which permits transition from an inhibited pattern to an agglutinated pattern is large. According to the method (B) of this invention, the margin of concentration for transition is clearly narrower than in the conventional method. In the method (A) of this invention, transition from an inhibited pattern to an agglutinated pattern is clearly noted with a concentration margin of 0.02 μg/ml. This effect is also considered to be due to the use of the water-soluble carboxyl-containing mono-olefinic polymeric compound.

In the conventional determination of haptens by a latex agglutination inhibiting reaction, an antibody to a hapten can be obtained for the first time by binding a strongly antigenic protein, etc. to the hapten and immunizing a mammal with the resulting bound product because the hapten itself does not have antigenicity. Thus, it has been considered to be essential to sensitize a latex with a product obtained by binding a hapten to a similar strongly antigenic protein, etc. In the present invention, binding to a strongly antigenic substance is essential as in conventional methods when preparing an antibody to a hapten. However, for binding to a latex a substantially immunologically inactive carboxyl-containing water-soluble mono-olefinic polymeric compound is used irrespective of the degree of its antigenicity. As a result, the aforesaid characteristics and advantages not seen in the prior art can be obtained. Furthermore, by using the corresponding antibody in the form bonded to the latex, or sensitizing the latex with the antibody, the utility of the antibody is further enhanced.

The following Referential Examples show that the water-soluble carboxyl-containing mono-olefinic polymeric compounds and the products obtained by binding haptens or their chemically modified products to these polymeric compounds as holders (component A-1) are substantially devoid of antigenicity, or are substantially inert immunologically.

Referential Example 1

Antigenicity of Holders (a) Immunization

As examples of the holder, polyacrylic acid (PAA for short) having a molecular weight of 2,000,000, polyacrylic acid having a molecular weight of 250,000, poly(sodium acrylate) (PAA.Na salt for short) having a molecular weight of about 1,500,000, and BSA (as a control) were each dissolved in an amount of 2 mg in 1 ml of physiological saline, and emulsified with the same amount of complete Freund's adjuvant. The emulsion was injected into the subcutaneous site and the paw of mature rabbits. The injection was performed eight times at two week intervals on groups each consisting of two rabbits. Blood letting was conducted on a trial basis from the test animals after three injections on the seventh day after each injection, and the sera were separated.

(b) Searching of Antibodies

Each of the sera obtained in (a) was tested to determine the presence of an antibody by a precipitation reaction in agar-gel in accordance with the Ouchterlony method and counter immunoelectrophoresis (CIE). The results are shown in Table 4. It is seen from the results that with BSA as a control, a clear precipitation pattern was seen to form in the sera obtained in all runs both by the Ouchterlony method and the counter immunoelectrophoresis, thus showing the formation of anti-BSA antibody. With PAA, however, no precipitation pattern was seen to form in any of the sera tested, and anti-PAA antibody was not detected.

TABLE 4

| Holder | Blood letting | Blood letting 1st | 2nd | 3rd | 4th | 5th | Total sera |
|---|---|---|---|---|---|---|---|
| PAA (MW: 2,000,000) | Ouchterlony | —* | — | — | — | — | — |
|  | CIE | — | — | — | — | — | — |
|  | Ouchterlony | — | — | — | — | — | — |
|  | CIE | — | — | — | — | — | — |
| PAA (MW: 250,000) | Ouchterlony | — | — | — | — | — | — |
|  | CIE | — | — | — | — | — | — |
|  | Ouchterlony | — | — | — | — | — | — |
|  | CIE | — | — | — | — | — | — |
| PAA.Na salt (MW: about 1,500,000) | Ouchterlony | — | — | — | — | — | — |
|  | CIE | — | — | — | — | — | — |
|  | Ouchterlony | — | — | — | — | — | — |
|  | CIE | — | — | — | — | — | — |
| BSA (FrV Fatty acid free) | Ouchterlony | +* | + | + | + | + | + |
|  | CIE | + | + | + | + | + | + |
|  | Ouchterlony | + | + | + | + | + | + |
|  | CIE | + | + | + | + | + | + |

—*: A precipitation pattern not formed.
+: A precipitation pattern formed.

The concentration of each of the holders and BSA in the Ouchterlony method and CIE was 5 mg/ml (Veronal buffer pH 8).

Referential Example 2

Antigenicity of a Hapten-Holder Bound Product (a) Immunization $E_3G$-polyacrylic acid (molecular weight 250,000) bound product produced by the same way as in Example 1 (e-3) given hereinbelow was used as an example of the hapten-holder bound product, and $E_3G$-BSA produced by the same way as in Example 1 (a) was used as a control.

Each of these products was dissolved in an amount of 2 mg in 1 ml of physiological saline, and emulsified with complete Freund's adjuvant. Each emulsion was subcutaneously administered to rabbits at the back. The injection was performed 10 times at two week intervals on groups each consisting of two rabbits. The blood was collected on a trial basis from the test animals after completing injection three times on the seventh day after each injection, and the sera were separated.

(b) Searching of Anti-$E_3G$ Antibody

Each of the sera obtained in (a) above was tested to defermine the presence of anti-$E_3G$ antibody by radio-immunoassay using $^3H$-$E_3G$. Each serum was diluted with a borate buffer (containing 0.06% BSA and 0.05% bovine gamma-globulin) having a pH of 8.0 to 10 times, 50 times, 100 times, and subsequently to dilute to 204,800 times by a multiple dilution method. The antibody titer was determined by the following method using the diluted sera.

10,000 dpm of a methanol solution of $^3H$-$E_3G$ was taken into a test tube, and evaporated to dryness in a stream of nitrogen. Then, 0.25 ml of each of the diluted sera obtained as described above was put into the test tube, and after shaking well, reacted at room temperature for 30 minutes. Then, 0.25 ml of saturated ammonium sulfate was added and mixed well with the reaction mixture. After standing for 10 minutes, the mixture was centrifuged for 10 minutes at a speed of 3,000 rpm. Then, 0.2 ml of the supernatant liquid was taken into a vial, and 10 ml of a dioxane scintillator was put into it. Radio-activity was measured by a liquid scintillation counter, and the ratio of $^3H$-$E_3G$ bonded was calculated.

In the groups given $E_3G$-BSA, the ratio of dilution of the serum which showed a bonding ratio of more than 70% at the time of blood letting was more than 3200. But in the groups to which $E_3G$-PAA was administered, the bonding ratio was only about 10% even when the serum was diluted to 10 times. This dilution ratio was about the same as that which was obtained when normal rabbit serum (NRS) was diluted similarly and reacted.

FIG. 1 attached to this application shows the titers of the anti-sera which were determined after 10 injections.

FIG. 1 attached to this application shows the titers of the antisera obtained from the blood samples which were collected after the 10th administration of $E_3G$-BSA and $E_3G$-PAA. The solid lines with circular marks show the titers of anti-$E_3G$-BSA antibody, and the broken lines show those of anti-$E_3G$-PAA antibody. The solid line with triangular marks shows the titer of NRS.

It is seen from the graph that the two rabbits to which $E_3G$-BSA was administered showed a high titer in both, but the two rabbits given $E_3G$-PAA did not show an increase in titer as obtained in the first blood collection, and the titer was much the same as that of NRS. It is concluded therefore that in the administration of $E_3G$-PAA, antibody to $E_3G$ (i.e., hapten) was not formed, and the carrier effect of PAA was not recognized.

Combination of Components A-2 and B-2

EXAMPLE 1

Determination of Estrogen in a Pregnant Woman Urine
(I)

(a) Production of Estriol 16-Glucuronide-BSA

Estriol 16-glucuronide (40 mg) was dissolved in 1 ml of N,N-dimethylformamide, and at less than 4° C., 20.6 microliters of tri-n-butylamine was added. Furthermore, 11.2 microliters of isobutyl chloroformate was added, and the mixture was stirred for 30 minutes. To the mixture was added a solution which had been prepared by adding 150 microliters of 1 N aqueous sodium hydroxide solution to a solution of 117 mg of BSA (bovine serum albumin) in 2.8 ml of water and then adding 2.0 ml of dimethylformamide and had been maintained at 8° C. The mixture was then stirred at 8° C., and one hour later, 16.6 microliters of 1 N aqueous sodium hydroxide solution was added. The mixture was further stirred for 3.5 hours. Then, on a column of Sephadex G-25, the unreacted estriol 16-glucuronide and low-molecular-weight reagents such as tri-n-butylamine were separated. The residue was dialyzed against purified water, and then lyophilized to afford estriol 16-glucuronide-BSA. When this lyophilized powder of antigen was examined by the Kober's reaction, it was confirmed that 27 to 30 moles of estriol 16-glucuronide were bound per mole of BSA.

(b) Production of Anti-Estriol 16-Glucuronide Antibody

Two milligrams of the estriol 16-glucuronide-BSA produced in (a) above was dissolved in 1 ml of physiological saline, and emulsified with the same amount of complete Freund's adjuvant. The emulsion was injected to the paw and subcutaneous site of mature rabbits. The injection was performed at one month intervals. After confirming the increase of the antibody titer, the total blood was collected and antiserum was obtained. The antiserum was immobilized at 56° C. for 30 minutes and caused to be absorbed by BSA. Subsequent salting out with ammonium sulfate afforded anti-estriol-16-glucuronide antibody.

(c) Production of a Latex Sensitized with Anti-Estriol 16-Glucuronide Antibody

Four milligrams of the anti-estriol 16-glucuronide antibody produced in (b) above was dissolved in 5 ml of a glycine-buffered sodium chloride solution, and 1 ml of a 10% polystyrene latex was added and mixed. The mixture was treated at 56° C. for 30 minutes. The treated mixture was then centrifuged. The precipitate was centrifugally washed with a glycine-buffered sodium chloride solution (pH 9.6). The precipitate was subpended in 15 ml of a glycine-buffered sodium chloride solution containing 0.05% of RSA (rabbit serum albumin) to prepare an anti-estriol 16-glucuronide antibody-sensitized polystyrene latex.

(d) Production of a Reactive Latex (d-1) Lysine-Latex

A solution of 260 mg of ε-tert.butoxycarbonyl lysine methyl ester in 3 ml of dimethylformamide was added to 5 ml of a 10% suspension of a carboxyl-modified polystyrene latex. The mixture was cooled to 0° C., and with stirring, 243 mg of 1-ethyl-3-(3-dimethylaminopropyl) carbodiimide hydrochloride (a water-soluble carbodiimide) was added. The mixture was stirred at 0° C. for 1 hour, and at room temperature for 3 hours. Then, the mixture was allowed to stand overnight at room temperature and then centrifuged. The supernatant liquid was discarded, and the precipitate was washed with a 50% aqueous solution of dimethylformamide and then with water.

Then, 5 ml of ice-cooled conc. hydrochloric acid was added, and the mixture was allowed to stand at 0° C. for 15 minutes with occasional shaking. It was then diluted with ice water to about 2 times and centrifuged. The precipitate was washed until the wash liquid became neutral. Then, 10 ml of a 10% aqueous solution of triethylamine was added. The mixture was stirred at room temperature for 15 minutes, centrifuged, and repeatedly washed with water until the wash liquid became neutral. Finally, the concentration of the resulting suspension was adjusted to 10% to form the desired lysine-latex. This product showed a positive result in a ninhydrin reaction. The product had the following structure.

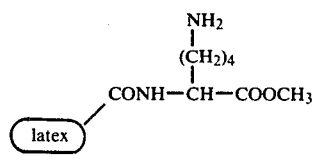

(d-2) Diaminoheptane-latex 2.5 ml of a 10% suspension of carboxyl-modified polystyrene latex was centrifuged, and 17.5 ml of a 0.01

M aqueous solution of aminoheptane was added to the precipitated latex to suspend it. The suspension was cooled to 4° C., and with stirring, 33.4 mg of 1-ethyl-3-(3-dimethylaminopropyl)carbodiimide hydrochloride was added. While the reaction temperature was maintained at 4° C., the mixture was stirred continuously overnight.

After the reaction, the reaction mixture was washed three times by centrifugation and floating in water. Finally, the concentration of the latex was adjusted to 10%. The product showed a positive result in a ninhydrin reaction. Its structural formula was as follows:

(e) Production of a Carboxyl-Containing Water-Soluble Mono-Olefinic Polymeric Compound combined with a chemically modified estrogen

(e-1) Production of Polyacrylic Acid Combined with 17-Amino-1,3,5(10)-Estratrien-3-ol The above aminosteroid (10.5 mg) and 100 mg of polyacrylic acid (average molecular weight of about 2,000,000) were dissolved in 5 ml of dimethylformamide, and 9 mg of dicyclohexyl carbodiimide (DCC) was added. The mixture was allowed to stand at room temperature for 30 hours.

The reaction mixture was transferred into a cellophane tube, and dialyzed against 2 liters of distilled water for 80 hours. The dialyzate was filtered, and the filtrate was concentrated to afford an aqueous solution of the above-captioned product.

When the aqueous solution was concentrated to 8.0 ml, it contained 1.26 mg/ml of the aminosteroid when determined with light having a wavelength of 280 m$\mu$.

(e-2) Production of a Vinylmethyl Ether/Maleic Anhydride Copolymer Combined with 17-Amino-1,3,5(10)-Estratrien-3-ol PVMMA (100 mg) was dissolved in 5 ml of dimethylformamide at an elevated temperature, and then 30 mg of the above-captioned aminosteroid was added. The resulting solution was allowed to stand at room temperature for 4 days.

The reaction mixture was transferred into a cellophane tube, and dialyzed against 2 liters of distilled water for 80 hours. The dialyzate was filtered. When the amount of the filtrate was adjusted to 50 ml, it contained 0.44 mg/ml of the aminosteroid when determined with light having a wavelength of 280 m$\mu$.

(e-3) Production of Polyacrylic Acid Combined with Estriol-16-Glucuronide (i) Estriol-16-Glucuronide-Lysine Derivative Estriol-16-glucuronide (232 mg) and 233 mg of $\epsilon$-benzyloxycarbonyl lysine methyl ester toluenesulfonate were dissolved in 15 ml of dimethylformamide, and with stirring under ice cooling, 164 mg of diphenyl phosphoryl azide and then 0.14 ml of triethylamine were added. After stirring for 1 hour at 0° C., the mixture was allowed to stand at room temperature for 48 hours. The reaction mixture was dried under reduced pressure at a temperature of below 40° C. The residue was subjected to preparative thin-layer chromatography to afford 240 mg (65% of theory) of the desired product having the following formula.

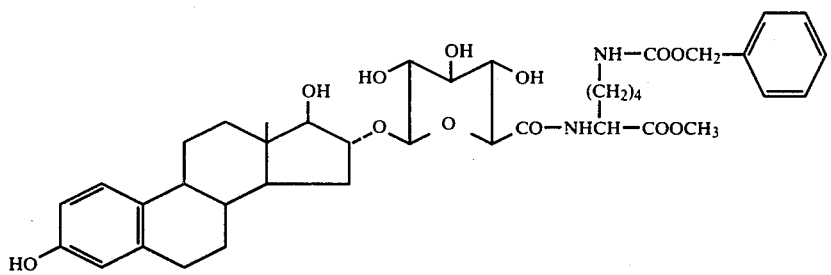

This product was not easily crystallized. It gave a single spot at Rf=0.55 (chloroform-methanol=5:1) in silica gel thin-layer chromatography, and colored violet by sulfuric acid and orange red by ninhydrin.

(ii) The estriol-16-glucuronide-lysine derivative (37 mg) obtained in (i) above was dissolved in 15 ml of a mixture of tertiary butanol and water (9:1), and 10 mg of 10% palladium-on-carbon was added. The mixture was stirred in a stream of hydrogen at room temperature and atmospheric pressure. When the reaction was traced by thin-layer chromatography, the starting material disappeared in 1.5 hours. Accordingly, the catalyst was separated by filtration, and the filtrate was washed. The filtrate and the wash liquid were dried under reduced pressure. The resulting product and 100 mg of polyacrylic acid were dissolved in 7 ml of dimethylformamide, and 12.4 mg of dicyclohexyl carbodiimide (DCC) was added. The mixture was allowed to stand for 48 hours at room temperature, and then treated in accordance with section (e-1) above to afford 10 ml of an aqueous solution of polyacrylic acid combined with estriol-16-glucuronide in an amount of 2.01 mg/ml.

(e-4) Production of Polyacrylic Acid Combined with Estriol-16-Glucuronide (II)

(i) Estriol-16-Glucuronide-Hexamethylenediamine Derivative

Estriol-16-glucuronide (93 mg) and 25 mg of N-hydroxysuccinimide were dissolved in 1.5 ml of dimethylformamide, and with stirring under ice cooling, 41 mg of DCC was added. After a lapse of 30 minutes, a solution of 55 mg of monobenzyloxycarbonyl hexamethylenediamine hydrochloride and 0.03 ml of triethylamine in 1 ml of dimethylformamide was added. The mixture was stirred for 2 hours under ice cooling, and for 12 hours at room temperature. Then, the mixture was evaporated to dryness under reduced pressure. The residue was subjected to preparative thin-layer chromatography to afford 82 mg (55% of theory) of the above-captioned product having the following structure.

(f-3) Production of a Latex Linked to PVMMA Combined with 17-Aminoestrogen

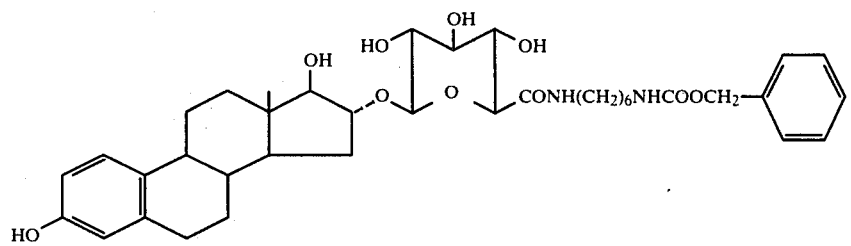

The captioned latex was produced in the same was as described in (f-1) using the lysine-latex produced in (d-1) and the 17-aminoestrogen-bound PVMMA produced in (e-2).

This product showed a single spot at Rf=0.42 (chloroform-methanol=5:1) in silica gel thin-layer chromatography.

(ii) Fifty milligrams of the estriol-16-glucuronidehexamethylenediamine derivative obtained in (i) above was dissolved in 3 ml of methanol, and 10 mg of palladium black was added. The mixture was stirred in a stream of hydrogen at room temperature and atmospheric pressure. The reaction ended in 2 hours. The catalyst was separated by filtration, and the filtrate was concentrated under reduced pressure. Addition of diethyl ether to the residue afforded 35 mg of the desired product with the splitting off of the carbobenzyloxy group.

Ten milligrams of this product and 100 mg of polyacrylic acid were dissolved in 2 ml of dimethylformamide, and 4 mg of DCC was added. The mixture was allowed to stand at room temperature for 50 hours. The reaction mixture was dialyzed, and the dialyzate was filtered and lyophilized to afford 95 mg of polyacrylic acid combined with estriol-16-glucuronide as a white powder.

(f) Production of a Latex Linked to a Carboxyl-Containing Mono-Olefinic Polymeric Compound Combined with a Chemically Modified Estrogen (f-1) Production of a Latex Linked to Polyacrylic Acid Combined with Estriol-16-Glucuronide The lysine-latex (0.1 g) produced in (d-1) above was suspended in 1 ml of distilled water, and 1 ml (corresponding to 0.3 mg of estriol-16-glucuronide) of polyacrylic acid combined with estriol-16-glucuronide which was produced in (e-3) above was added. Then, 10 mg of 1-ethyl-3-(3-dimethylaminopropyl)carbodiimide hydrochloride was added. With stirring, the reaction was performed overnight. After the reaction, the reaction mixture was centrifuged, and the resulting precipitate was washed three times with 10 ml of a glycine-buffered sodium chloride solution. The precipitate was suspended in 30 ml of a glycine-buffered sodium chloride solution containing 0.05% RSA (rabbit serum albumin) to produce a latex linked to polyacrylic acid combined with estriol-16-glucuronide.

(f-2) Production of a Latex Linked to Polyacrylic Acid Combined with 17-Aminoestrogen The captioned latex was produced by the same way as described in (f-1) using the lysine-latex produced by the method described in (d-1) and polyacrylic acid combined with 17-aminoestrogen produced by the method described (e-1).

(f-4) Production of a Latex Linked to Polyacrylic Acid Having Estriol-16-Glucuronide Bound Thereto The captioned latex was produced in the same way as in (f-1) using the diaminoheptane-latex produced in (d-2) and the polyacrylic acid having estriol-16-glucuronide bound thereto produced in (e-4).

(g) Determination of Urinary Estrogen

Five assay samples of urine taken from pregnant women were diluted to 50, 100, 200, and 400 times. One drop (0.03 ml) of each diluted urine sample was droped onto a slide. Then, one drop of the latex sensitized with anti-estriol-16-glucuronide antibody produced in (e) was added. One drop of the latex linked to polyacrylic acid having estriol-16-glucuronide bound thereof produced in (f-1) was further added. The three were mixed uniformly and shaken for 2 minutes. Then, the agglutinated pattern and the agglutination inhibited pattern were examined with the naked eye.

In this Example, the assay sensitivity of the reagent was adjusted to 0.1 μg/ml. Thus, the estrogen concentration in each urine sample was as shown in Table 5.

TABLE 5

| Sample No. | Ratio of dilution | | | | Amount of estrogen (μg/ml) |
| --- | --- | --- | --- | --- | --- |
| | 50 | 100 | 200 | 400 | |
| 1 | ++ | ++ | − | − | 10 |
| 2 | ++ | − | − | − | 5 |
| 3 | ++ | ++ | ++ | − | 20 |
| 4 | ++ | ++ | − | − | 10 |
| 5 | ++ | ++ | ++ | − | 20 |

Standards of determination:-
−: a clear agglutinated pattern
++: a completely agglutination-inhibited pattern The same standards of determination will apply to the following Examples.

When the products obtained in (f-2), (f-3), and (f-4) were used as the latex linked to a modified estrogen-bound carboxyl-containing mono-olefinic polymer, the same results were obtained as in the case of using (f-1).

EXAMPLE 2

Determination of Urinary Pregnanediol (a) Production of Pregnanediol-3-glucuronide-BSA This product was prepared in the same way as in Example 1, (a) using pregnanediol-3-glucuronide and BSA.

(b) Production of Anti-Pregnanediol-3-Glucuronide Antibody

The captioned antibody was produced by using the pregnanediol-3-glucuronide-BSA produced in (a) above, immunizing a goat with it in the same way as in Example 1, (b), and collecting antiserum.

(c) Production of a Latex Sensitized with Anti-Pregnanediol-3-Glucuronide Antibody The captioned polystyrene latex was produced in the same way as in Example 1, (c) using the anti-pregnanediol-3-glucuronide antibody produced in (b) above.

(d) Production of PVMMA Combined with Pregnanediol-3-Glucuronide (i) Pregnanediol-3-Glucuronide-Lysine Derivative Pregnanediol-3-glucuronide (99 mg) and 140 mg of ε-benzyloxycarbonyl lysine methyl ester toluenesulfonate were dissolved in 12 ml of dimethylformamide, and with stirring under ice cooling, 65 mg of diphenyl phosphoryl azide and 0.056 ml of triethylamine were added. The mixture was treated in the same way as in Example 1, (e-3) to afford 100 mg (58% of theory) of the desired lysine derivative having the following structural formula.

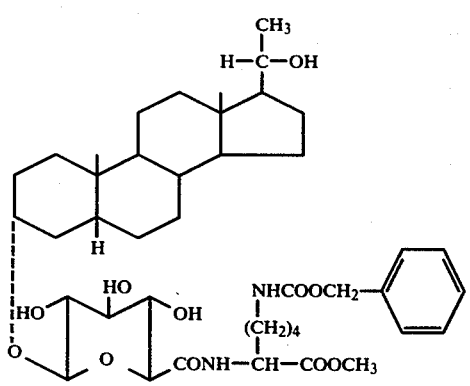

(ii) The pregnanediol-3-glucuronide-lysine derivative (38 mg) obtained in (i) above was catalytically reduced by the same way as in Example 1, (e-3). The product and 100 mg of PVMMA were dissolved in 6 ml of dimethylformamide at an elevated temperature, and the solution was allowed to stand at room temperature for 4 days. The reaction mixture was treated in the same way as in Example 1, (e-2) to afford 30 ml of a solution of PVMMA combined with pregnanediol-3-glucuronide which had a pregnanediol content of 0.46 mg/ml as determined by coloration with sulfuric acid.

(e) Production of a Latex Linked to PVMMA Combined with Pregnanediol-3-Glucuronide The captioned latex was produced in the same way as in Example 1, (f) using the lysine-latex produced in Example 1, (d-1) and the PVMMA combined with pregnanediol-3-glucuronide produced in (d) above.

(f) Determination of Urinary Pregnanediol

Five assay samples of urine taken from pregnant women were each diluted to 50, 100, 200, 400, and 800 times with a glycine-buffered sodium chloride solution. The urinary pregnanediol was determined by the same procedure as in Example 1, (g) using (c) and (e) above.

Since in this Example, the assay sensitivity of the reagent was adjusted to 0.05 μg/ml, the concentration of pregnanediol of each urin sample was as shown in Table 6.

TABLE 6

| Sample No. | Ratio of dilution | | | | | Amount of pregnanediol (μg/ml) |
| --- | --- | --- | --- | --- | --- | --- |
| | 50 | 100 | 200 | 400 | 800 | |
| 1 | ++ | ++ | ++ | − | − | 10 |
| 2 | ++ | − | − | − | − | 2.5 |
| 3 | ++ | ++ | ++ | ++ | − | 20 |
| 4 | ++ | ++ | − | − | − | 5 |
| 5 | ++ | ++ | ++ | − | − | 10 |

EXAMPLE 3

Measurement of Urinary Pregnanetriol (a) Production of Pregnanetriol-3-Glucuronide-BSA Pregnanetriol-3-glucuronide-BSA was produced by the same way as in Example 1, (a) using pregnanetriol-3-glucuronide and BSA.

(b) Production of Anti-Pregnanetriol-3-Glucuronide Antibody

The captioned antibody was produced by using the pregnanetriol-3-glucuronide-BSA produced in (a) above and immunizing a rabbit with it in the same way as in Example 1, (b).

(c) Preparation of a Latex Sensitized with Antipregnanetriol-3-Glucuronide Antibody The captioned polystyrene latex was produced in the same way as in Example 1, (c) using the anti-pregnanetriol-3-glucuronide antibody produced in (b) above.

(d) Production of Polyacrylic Acid Combined with Pregnanetriol-3-Glucuronide

Pregnanetriol-3-Glucuronide-Hexamethylenediamine Derivative

Pregnanetriol-3-glucuronide (102 mg) and 63 mg of monobenzyloxycarbonyl hexamethylenediamine hydrochloride were dissolved in 4 ml of dimethylformamide, and after cooling with ice, 55 mg of diphenyl phosphoryl azide and 0.06 ml of triethylamine were added with stirring. The mixture was stirred at 0° C. for 2 hours, and then allowed to stand at room temperature for 72 hours. The reaction mixture was evaporated to dryness under reduced pressure. The remaining product was subjected to preparative thin-layer chromatography to afford 61 mg (41% of theory) of the desired pregnanetriol-3-glucuronide-hexamethylenediamine derivative.

(ii) The pregnanetriol-3-glucuronide-hexamethylenediamine derivative (56 mg) obtained in (i) above was catalytically reduced in the same way as in Example 1, (e-4). The product and 200 mg of polyacrylic acid were dissolved in 20 ml of dimethylformamide, and 16 mg of DCC was added. The mixture was allowed to stand at room temperature for 5 days. The reaction mixture was treated in the same way as in Example 1, (e-4) to afford 168 mg of polyacrylic acid combined with pregnanetriol-3-glucuronide as a white powder.

(e) Production of a Latex Linked to Polyacrylic Acid Combined with Pregnanetriol-3-Glucuronide The captioned latex was produced in the same way as in Example 1, (f) using the lysine-latex produced in Example 1, (d-1) and the polyacrylic acid with pregnanetriol-3-glucuronide produced in (d) above.

(f) Determination of Urinary Pregnanetriol

Absorbent tampons of a certain fixed size were applied to the urine of neonates or infants or to diapers to get the urine adsorbed therein. These tampons were dried, and then leached with a predetermined amount of distilled water to prepare assay samples. The assay samples were diluted with physiological saline to 25, 50, 100, 200, and 400 times calculated on the basis of the original urine. The urinary pregnanetriol was determined by the same procedure as in Example 1, (g) using the products (c) and (e) above. Since in this Example, the assary sensitivity of the reagent was adjusted to 0.1 μg/ml, the amount of pregnanetriol in each of the assay samples was as shown in Table 7.

TABLE 7

| Sample No. | Ratio of dilution | | | | | Amount of prognanetriol (μg/ml) | Evaluation |
|---|---|---|---|---|---|---|---|
| | 25 | 50 | 100 | 200 | 400 | | |
| A | − | − | − | − | − | <2.5 | Normal |
| B | ++ | − | − | − | − | 2.5 | " |
| C | − | − | − | − | − | <2.5 | " |
| D | − | − | − | − | − | <2.5 | " |
| E | ++ | ++ | ++ | ++ | ++ | >40 | Suprarenal hyperplasia |

As shown in Table 7, this test permits the detection of cogenital suprarenal hyperplasia which a neonate has. Thus, by treatment with an adrenal cortical hormone at the early stage, the neonate suffering from it can grow normally. If it is a girl, she can grow up into a woman who can be pregnant and deliver normally.

EXAMPLE 4

Determination of Urinary 17-OHCS (a) Production of 3α, 11β, 17α, 21-Tetrahydroxypregnan-2-one(THF) 3-Glucuronide-BSA THF-3-glucuronide-BSA was produced by the same way as in Example 1, (a) using THF 3-glucuronide and BSA.

(b) Production of Anti-THF 3-Glucuronide Antibody

The captioned antibody was produced by using the THF 3-glucuronide-BSA produced in (a) above, and immunizing a rabbit with it in the same way as in Example 1, (b).

(c) Production of a Latex Sensitized with Anti-THF-3-Glucuronide Antibody

The captioned polystyrene latex was produced in the same way as in Example 1, (c) using the Anti-THF-3-glucuronide antibody produced in (b) above.

(d) Production of Polyacrylic Acid Combined with THF 3-glucuronide (i) THF 3-Glucuronide-Lysine Derivative The desired lysine derivative was produced in accordance with the method described in Example 1, (e-3) from 53 mg of THF 3-glucuronide, 59 mg of ε-benzyloxycarbonyl lysine methyl ester toluenesulfonate, 33 mg of diphenyl phosphoryl azide and 0.027 ml of triethylamine. Yield 57 mg; (theoretical yield 71%)

(ii) Forty milligrams of the lysine derivative obtained in (i) above was catalytically reduced by the same way as in Example 1, (e-3), and then reacted with 14 mg of DCC and 100 mg of polyacrylic acid. The reaction mixture was after-treated to afford 15 ml (THF content 0.96 mg/ml) of a solution of polyacrylic acid combined with THF 3-glucuronide.

(e) Production of a Latex Linked to THF 3-Glucuronide Combined with Polyacrylic Acid The captioned latex was produced by the same way as in Example 1, (f) using the diaminoheptane latex produced in Example 1, (d-2) and the polyacrylic acid combined with THF 3-glucuronide produced in (d) above.

(f) Determination of Urinary 17-OHCS

Urine of a normal healthy man and urine of a normal healthy woman were each diluted with a glycine-buffered sodium chloride solution to 10, 15, 20, 25, 30, and 40 times respectively. Using the above products (c) and (e), urinary 17-OHCS was determined by the same procedure as in Example 1, (g). The results are shown in Table 8.

Since in this Example, the assay sensitivity of the reagent was adjusted to 0.2 μg/ml, it was found that the urine of the healthy man contained 5 μg/ml of 17-OHCS, and the urine of the healthy woman contained 4 μg/ml of 17-OHCS.

TABLE 8

| Urine | Ratio of dilution | | | | | | Concentration of 17-OHCS in urine (μg/ml) |
|---|---|---|---|---|---|---|---|
| | 10 | 15 | 20 | 25 | 30 | 40 | |
| Healthy man | ++ | ++ | ++ | ++ | − | − | 5 |
| Healthy woman | ++ | ++ | ++ | − | − | − | 4 |

EXAMPLE 5

Determination of Morphine (a) Production of Carboxymethyl Morphine-BSA

BSA (100 mg) was dissolved in 25 ml of distilled water, and 80 mg of carboxymethyl morphine was dissolved in the resulting solution. The solution was adjusted to pH 5.5, and 80 mg of 1-ethyl-3-(3-dimethylaminopropyl)carbodiimide hydrochloride was dissolved in the solution. The solution was stirred at room temperature overnight to perform the reaction. The reaction mixture was dialyzed against distilled water. The dialyzate was lyophilized to afford carboxylmethyl morphine-BSA.

(b) Production of Anti-carboxylmethyl Morphine Antibody

Anti-carboxymethyl morphine antibody was produced by using the carboxymethyl morphine-BSA produced in (a) above, immunizing a rabbit with it by the same way as in Example 1, (b), and collecting antiserum.

(c) Production of a Latex Sensitized with Anti-Carboxymethyl Morphine Antibody

The captioned sensitized latex was produced in the same way as in Example 1, (c) using the anti-carboxylmethyl morphine antibody produced in (b) above.

(d) Production of Polyacrylic Acid Combined with Carboxymethyl Morphine (i) Carboxymethyl Morphine-Lysine Derivative In the same way as in Example 1, (e-3), 66.7 mg (78% of theory) was produced from 51.5 mg of carboxymethyl morphine, 61 mg of ε-tert-butoxycarbonyl lysine methyl ester acetate, 10 ml of dimethylformamide, 49 mg of diphenyl phosphoryl azide and 0.042 ml of triethylamine.

(ii) Forty milligrams of the lysine derivative obtained in (i) was dissolved in 5 ml of 98% formic acid. The solution was allowed to stand at room temperature for 2 hours, and then evaporated to dryness under reduced pressure below 40° C. The residue was maintained under reduced pressure on potassium hydroxide for 24 hours, and then dissolved in 5 ml of dimethylformamide. Triethylamine (0.02 ml) was added, and 100 mg of polyacrylic acid and 3 ml of dimethylformamide were added. Further, 21 mg of DCC was added, and the reaction was performed for 48 hours. The reaction mixture was treated by the same way as in Example 1, (e-3) to afford 10 ml (carboxymethyl morphine content 2.0 mg/ml) of a solution of polyacrylic acid combined with carboxymethyl morphine.

(e) Production of a Latex Linked to Polyacrylic Acid Combined with Carboxymethyl Morphine A latex linked to polyacrylic acid combined with carboxymethyl morphine was produced by the same way as in Example 1, (f) using the lysine-latex produced in Example 1, (d-1) and the polyacrylic acid combined with carboxymethyl morphine produced in (d) above.

(f) Determination of Morphine

Morphine was dissolved in physiological saline and morphine-free urine to the concentrations shown in Table 9. Morphine was determined by the same procedure as in Example 1, (g) using the products (c) and (e) above. The results are shown in Table 9. The assay sensitivity of the reagent in this Example was 50 ng/ml. It was found that this sensitivity was not affected by the urine components.

TABLE 9

| Solvent | Concentration of morphine (ng/ml) | | | | |
|---|---|---|---|---|---|
| | 0 | 25 | 50 | 100 | 200 |
| Physiological saline | − | − | ++ | ++ | ++ |
| Morphine-free urine of a male | − | − | ++ | ++ | ++ |

EXAMPLE 6

Determination of Thyroxine (T$_4$)

(a) Production of Thyroxine-BSA

BSA (50 mg) was dissolved in 25 ml of distilled water, and a solution of thyroxine in 5 ml of dimethylformamide was added to the solution. With stirring, 30 mg of 1-cyclohexyl-3-(2-morpholinyl-4-ethyl)carbodiimide metho-p-toluenesulfonate was added. The reaction was performed overnight at room temperature. The reaction mixture obtained was dialyzed against distilled water, and lyophilized to produce thyroxine-BSA.

(b) Production of Anti-Thyroxine Antibody

Anti-thyroxine antibody was produced by using the thyroxine-BSA produced in (a) above, immunizing a rabbit with it, and collecting antiserum.

(c) Production of a Latex Linked to Anti-Thyroxine Antibody

Five milligrams of the anti-thyroxine antibody produced in (b) above was dissolved in 5 ml of distilled water, and mixed with 1 ml of a 10% suspension of a carboxyl-modified latex. Then, 10 mg of 1-ethyl-3-(3-dimethylaminopropyl)carbodiimide hydrochloride was added, and the reaction was performed overnight with stirring. After the reaction, the reaction mixture was centrifuged. The resulting precipitate was washed with a glycine-buffered sodium chloride solution. The precipitate was suspended in 15 ml of a glycine-buffered sodium chloride solution containing 0.08% of rabbit serum albumin to produce a latex linked to anti-thyroxine antibody.

(d) Production of Vinyl Methyl Ether/Maleic Anhydride Copolymer (PVMMA) Combined with Thyroxine In the same way as in Example 1, (e-2), the above product was prepared from PVMMA and thyroxine. By lyophilizing the dialyzate, the product was obtained as a white powder.

(e) Production of a Latex Linked to PVMMA Combined with Thyroxine

The captioned latex was produced in the same way as in Example 1, (f) using the PVMMA combined with thyroxine produced in (d) above and the lysine-latex produced in Example 1, (d-1).

(f) Determination of T$_4$

8-Anilino-1-naphthalenesulfonic acid was added to 4 assay samples of urine taken from normal healthy males. Each of the mixtures was diluted with physiological saline to 1.5, 2 and 3 times, and T$_4$ was determined by the same procedure as in Example 1, (g). Since the assay sensitivity of the reagent in this Example was adjusted to 30 ng/ml, the measured T$_4$ concentrations were as shown in Table 10.

TABLE 10

| Sample No. | Ratio of dilution | | | | Concentration of T$_4$ (ng/ml) |
|---|---|---|---|---|---|
| | 0 | 1.5 | 2 | 3 | |
| 1 | ++ | ++ | − | − | 45 |
| 2 | ++ | − | − | − | 30 |
| 3 | ++ | ++ | − | − | 45 |
| 4 | ++ | ++ | − | − | 45 |

EXAMPLE 7

Determination of Catecholamine (a) Production of Metanephrine-BSA

Metanephrine-BSA was produced in the same way as in Example 1, (a) using metanephrine and BSA.

(b) Production of Anti-metanephrine Antibody

Anti-metanephrine antibody was produced by using the metanephrine-BSA produced in (a) above, immunizing a rabbit with it in the same way as in Example 1, (b), and collecting antiserum.

(c) Production of a Latex Sensitized with Anti-metanephrine Antibody

The captioned latex was produced in the same way as in Example 1, (c) using the anti-metanephrine antibody produced in (b) above.

(d) Production of Polyacrylic Acid Combined with Metanephrine

Polyacrylic acid combined with metanephrine was produced from polyacrylic acid and metanephrine in the same way as in Example 1, (e-1).

(e) Production of a Latex Linked to Metanephrine-Bound Polyacrylic acid

A latex linked to polyacrylic acid combined with metanerphrine was produced in the same way as in Example 1, (f) using the lysine-latex produced in Example 1, (d-1) and the polyacrylic acid combined with metanephrine produced in (d) above.

(f) Determination of Metanephrine

Three assay samples of urine from normal healthy males were each diluted with physiological saline to 1.5, 2, and 3 times, and urinary metanephrine was determined by the same procedure as in Example 1, (g). Since in this Example, the assay sensitivity of the reagent was adjusted to 20 ng/ml, the measured concentrations were as shown in Table 11.

TABLE 11

| Sample No. | Ratio of dilution | | | | Concentration of metanephrine (ng/ml) |
|---|---|---|---|---|---|
| | 0 | 1.5 | 2 | 3 | |
| 1 | ++ | ++ | − | − | 30 |
| 2 | ++ | ++ | ++ | − | 40 |
| 3 | ++ | ++ | ++ | − | 40 |

Combination of Component A-1 with Component B-2

EXAMPLE 8

Determination of Urinary Estrogen (I)

Five assay samples of urine taken from pregnant women were each diluted with a glycine-buffered sodium chloride solution to 50, 100, 200, and 400 times respectively. One drop (0.03 ml) of each diluted urine was added to a reaction slide. One drop of the latex sensitized with anti-estriol 16-glucuronide antibody produced in Example 1, (c) was added to it. After mixing, one drop of a solution of the polyacrylic acid combined with 17-amino-1,3,5(10)-estratrien-3-ol produced in Example 1, (e-1) having an estrogen concentration of 12 mg/ml was added dropwise. The three were uniformly mixed, and shaken for 2 minutes. The agglutinated pattern and the agglutination-inhibited pattern were observed with the naked eye. Since in this Example, the assay sensitivity of the reagent was adjusted to 0.1 μg/ml, the concentration of estrogen in each urine sample was as shown in Table 12.

TABLE 12

| Sample No. | Ratio of dilution | | | | Amount of estrogen (μg/ml) |
|---|---|---|---|---|---|
| | 50 | 100 | 200 | 400 | |
| 1 | ++ | ++ | − | − | 10 |
| 2 | ++ | − | − | − | 5 |
| 3 | ++ | ++ | ++ | − | 20 |
| 4 | ++ | ++ | − | − | 10 |
| 5 | ++ | ++ | ++ | − | 20 |

When the products obtained in Example 1, (e-2), (e-3) and (e-4) were used as the carboxyl-containing monoolefinic polymeric compound combined with modified estrogen in the above example, similar results to those in the case of using (e-1) were obtained.

EXAMPLE 9

Determination of Urinary Estrogen (II)

(a) Production of Erythrocytes Sensitized with Anti-estriol 16-Glucuronide Antibody To a 4% suspension of formalin-fixed goat erythrocytes (phosphoric acid-buffered sodium chloride solution, pH 6.4) was added an equal volume of a 0.01% tannic acid solution, and they were reacted at 56° C. for 30 minutes. Then, the erythrocytes were washed with a phosphoric acid-buffered sodium chloride solution to form an 8% suspension. Then, an equal volume of a 0.05% solution of the anti-estriol-16-glucuronide antibody produced in Example 1, (b) was added, and reacted at 56° C. for 2 hours. After the reaction, the red cells were centrifugally washed with a phosphoric acid-buffered sodium chloride solution, and then diluted to a concentration of 1.5% (cell concentration) with a phosphoric acid-buffered sodium chloride solution containing 0.2% NRS (normal rabbit serum) and 5% of lactose. The dilution was poured in an amount of 0.1 ml in each of ampoules, and then lyophilized to afford erythrocytes sensitized with anti-estriol 16-glucuronide antibody.

(b) Determination of Urinary Estrogen (II)

Urine samples taken from healthy females at various stages of the menstrual cycle were each diluted with a phosphate-buffered sodium chloride solution to 5, 10, 20, 40 and 80 times. Each of the urine dilutions was poured in an amount of 0.1 ml into each of round-bottomed small test tubes. Then, one ampoule of the erythrocytes sensitized with anti-estriol 16-glucuronide antibody produced in (a) above was suspended in 0.3 ml of a phosphate bufferized sodium chloride solution. The suspension was added to each of the urine dilution in each test tube, and mixed with stirring. Then, 0.1 ml of the solution of polyacrylic acid combined with 17-amino-1,3,5(10)-estratrien-3-ol produced in Example 1, (e-1) was added. The mixture was well stirred, and allowed to stand for 2 hours on a stand equipped with a mirror. The presence of estrogen was determined by the pattern formed on the bottom of the test tube. Since in this Example, the assay sensitivity of the reagent was adjusted to 2 ng/ml, the urinary estrogen concentration of each urine sample was as shown in Table 13.

TABLE 13

| Menstrual cycle | Ratio of dilution of urine | | | | | Concentration of estrogen in the urine (ng/ml) |
|---|---|---|---|---|---|---|
| | 5 | 10 | 20 | 40 | 80 | |
| Follicular stage | ++ | − | − | − | − | 10 |
| Ovulating stage | ++ | ++ | ++ | ++ | − | 80 |
| Luteal stage | ++ | ++ | − | − | − | 20 |

EXAMPLE 10

Determination of Urinary Pregnanediol

Five assay samples of urine taken from pregnant women were each diluted with a glycine-buffered sodium chloride solution to 50, 100, 200, 400 and 800 times, and the urinary pregnanediol was determined by the same procedure as in Example 8 using the products obtained in Example 2, (c) and (d). Since in this Example, the assay sensitivity of the reagent was adjusted to 0.05 μg/ml, the pregnanediol concentrations of the assay samples were as shown in Table 14.

TABLE 14

| Sample No. | Ratio of dilution | | | | | Amount of pregnanediol (μg/ml) |
|---|---|---|---|---|---|---|
| | 50 | 100 | 200 | 400 | 800 | |
| 1 | ++ | ++ | ++ | − | − | 10 |
| 2 | ++ | − | − | − | − | 2.5 |
| 3 | ++ | ++ | ++ | ++ | − | 20 |
| 4 | ++ | ++ | − | − | − | 5 |
| 5 | ++ | ++ | ++ | − | − | 10 |

EXAMPLE 11

Determination of Thyroxine ($T_4$)

Four samples of sera of normal healthy males were diluted with physiological saline to 1.5, 2 and 3 after adding 8-anilino-1-naphthalenesulfonic acid. Using the products obtained in Examples 4, (c) and (d), thyroxine ($T_4$) was determined by the same procedure as in Example 8.

Since, in this Example, the assay sensitivity of the reagent was adjusted to 30 ng/ml, the measured concentrations of $T_4$ in the sera were as shown in Table 15.

TABLE 15

| Sample No. | Ratio of dilution | | | | Concentration of $T_4$ (ng/ml) |
|---|---|---|---|---|---|
| | 0 | 1.5 | 2 | 3 | |
| 1 | ++ | ++ | − | − | 45 |
| 2 | ++ | − | − | − | 30 |
| 3 | ++ | ++ | − | − | 45 |
| 4 | ++ | ++ | − | − | 45 |

EXAMPLE 12

Determination of Urinary Pregnanetriol

Absorbent tampons of a predetermined size were applied to the urine of neonates or infants or to diapers to get the urine adsorbed therein. They were dried, and then leached with a predetermined amount of distilled water to prepare an assay samples. The assay samples were each diluted with physiological saline to 25, 50, 100, 200, and 400 times calculated on the original urine. Using the products obtained in Example 3, (c) and (d), the urinary pregnanetriol was determined by the same procedure as in Example 8. Since in this Example, the sensitivity of the reagent was adjusted to 0.1 μg/ml, the amounts of pregnanetriol in the samples were as shown in Table 16.

TABLE 16

| Sample | Ratio of dilution | | | | | Amount of pregnanetriol (μg/ml) | Evaluation |
|---|---|---|---|---|---|---|---|
| | 25 | 50 | 100 | 200 | 400 | | |
| A | − | − | − | − | − | 2.5 | Normal |
| B | ++ | − | − | − | − | 2.5 | " |
| C | − | − | − | − | − | 2.5 | " |
| D | − | − | − | − | − | 2.5 | " |
| E | ++ | ++ | ++ | ++ | ++ | 40 | Suprarenal hyperplasia |

As shown in Table 16, this test permits the detection of congenital suprarenal hyperplasia which a neonate has. Thus, by treatment with an adrenal cortex hormone at the early stage, the neonate suffering from it can grow up normally. If it is a girl, she can grow up into a woman who can be pregnant and deliver normally.

EXAMPLE 13

Determination of 17-KS (a) Production of Etiocholanolone Hemisuccinate-BSA

Etiocholanolone hemisuccinate BSA was produced in the same way as in Example 1, (a) from ethiochloanolone hemisuccinate.

(b) Production of Anti-Etiocholanolone Hemisuccinate Antibody

The captioned antibody was produced by using the etiocholanolone hemisuccinate BSA produced in (a) above, and immunizing a rabbit with it in by the same way as in Example 1, (b).

(c) Production of a Latex Linked to Anti-Etiocholanolone Hemisuccinate Antibody

The captioned latex was produced by the same way as in Example 6, (c) using the anti-etiocholanolone hemisuccinate antibody produced in (b) above.

(d) Production of Ethiocholanolone Hemisuccinate-bound Polyacrylic Acid (i) Etiocholanolone Hemisuccinate-Lysine Derivative Etiocholanolone hemisuccinate (78 mg), 64 mg of ε-tert-butoxycarbonyllysine methyl ester acetic acid salt and 25 mg of N-hydroxysuccinimide were dissolved in 2 ml of methylformamide. Then, 0.08 ml of triethylamine was added, and the mixture was cooled with ice. With stirring, 41 mg of DCC was added. The reaction was performed for 3 hours under ice cooling, and then for 10 hours at room temperature. The reaction mixture was evaporated to dryness under reduced pressure. The residue was purified by preparative thin-layer chromatography to afford 64 mg (51% of theory) the desired product of the following structure.

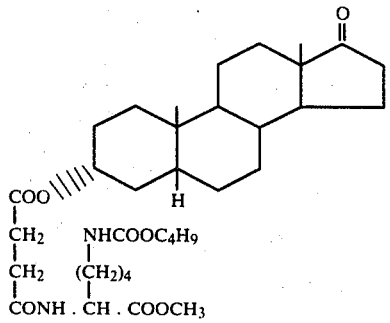

```
         COO\\\       H
          |
         CH2    NHCOOC4H9
          |       |
         CH2    (CH2)4
          |       |
         CONH . CH . COOCH3
```

This product gave a single spot at Rf=0.64 (chloroform-methanol=10:1) in silica gel thin-layer chromatography.

(ii) Thirty milligrams of the etiocholanolone hemisuccinate-lysine derivative obtained in (i) above was dissolved in 8 ml of 98% formic acid. The solution was allowed to stand at room temperature for 8 hours, and then evaporated to dryness under reduced pressure at less than 45° C. The product and 100 mg of polyacrylic acid were dissolved in 5 ml of dimethylformamide, and 0.03 ml of triethylamine was added. Then, 20 mg of DCC was added, and the mixture was allowed to stand at room temperature for 50 hours. The reaction mixture was treated in the same way as in the last half of Example 1, (e-3), (ii) to afford 100 mg of polyacrylic acid combined with etiocholanolone hemisuccinate (white powder).

(e) Deetermination of Urinary 17-KS

Two assay samples of urine taken from normal healthy males were each diluted with a phosphate-buffered sodium chloride solution, and urinary 17-KS was determined in the same way as in Example 8 using the latex linked to anti-etiocholanolone hemisuccinate antibody produced in (c) above and the polyacrylic acid combined with etiocholanolone hemisuccinate produced in (d) above. The assay sensitivity was adjusted to 0.5 µg/ml. It was found that the two samples each contained 4.0 µg/ml of 17-KS.

EXAMPLE 14

Determination of Morphine (a) Production of Erythrocytes Sensitized with Anti-Carboxymethyl Morphine Antibody Erythrocytes sensitized with anti-carboxymethyl morphine antibody were produced in the same way as in Example 9, (a) using the anti-carboxymethyl morphine antibody produced in Example 5, (b).

(b) Determination of Morphine

Morphine was dissolved in physiological saline and morphine-free urine to the concentration shown in Table 17, and morphine was determined by the same procedure as in Example 9, (b) using the products obtained in (a) above and Example 5, (d). The results are shown in Table 17. The assay sensitivity of the reagent in this Example was 50 ng/ml, and it was found that this sensitivity was not affected by the urine components.

TABLE 17

| Solvent | Concentration of morphine (ng/ml) | | | | |
|---|---|---|---|---|---|
| | 0 | 25 | 50 | 100 | 200 |
| Physiological saline | − | − | ++ | ++ | ++ |
| Morphine-free urine | − | − | ++ | ++ | ++ |

Also, with a reagent containing both a latex sensitized with the anti-carboxymethylmorphine and PAA combined with carboxymethylmorphine which has the same assay sensitivity as that of the reagent obtained by Example 14 (a) and (b), similar results were obtained.

EXAMPLE 15

Determination of Metanephrine

Three assay samples of urine taken from normal healthy males were each diluted to 1.5, 2 and 3 times with physiological saline, and urinary metanephrine was determined by the same procedure as in Example 8 using the products obtained in Example 7, (c) and (d). Since the assay sensitivity of the reagent in this Example was adjusted to 20 ng/ml, the measured concentrations of metanephrine in the urine were as shown in Table 18.

TABLE 18

| Sample No. | Ratio of dilution | | | | Concentration of metanephrine (ng/ml) |
|---|---|---|---|---|---|
| | 0 | 1.5 | 2 | 3 | |
| 1 | ++ | ++ | − | − | 30 |
| 2 | ++ | ++ | ++ | − | 40 |
| 3 | ++ | ++ | ++ | − | 40 |

Combination of Component A-2 with Component B-1

EXAMPLE 16

Determination of Urinary 17-KS (a) Production of a Latex Linked to Polyacrylic Acid Combined with Etiocholanolone Hemisuccinate A lated linked to polyacrylic acid combined with eticholanolone hemisuccinate was produced in the same way as in Example 1, (f) using the lysine-latex produced in Example 1, (d-1) and the polyacrylic acid combined with etiocholanolone hemisuccinate produced in Example 13, (d).

(b) Determination of Urinary 17-KS

The antibody produced in Example 13, (d) was diluted with a glycine-buffered sodium chloride solution, and by using the latex obtained in (a) above, urinary 17-KS was determined while the assay sensitivity of the reagent was adjusted to 0.5 µg/ml. Two assay samples of urine taken from normal healthy males were each diluted with a phosphate-buffered sodium chloride solution to 2, 4, 8 and 16 times. Urinary 17-KS was determined in the same way as in Example 1, (g) using the aforesaid diluted antibody instead of the antibody-sensitized latex in Example 1, (g). It was found that both of these assay samples contained 4.0 µg/ml of 17-KS.

What is claimed is:

1. An immunochemical assay reagent comprising a combination of (A-1) a carboxyl-containing water-soluble mono-olefinic polymeric compound chemically bound with a hapten or a hapten which is chemically modified to chemically bind it with said polymeric compound and (B-2) the antibody to said hapten supported on a carrier, said carrier being sensitized or chemically bound with said hapten antibody, the components of said combination being physically separated from each other until used for determining the presence of a hapten in an assay sample.

2. An immuno assay reagent comprising a combination of (A-2) a hapten-supported latex obtained by chemically combining a polymeric latex having a particle diameter of about 0.01 to about 2 microns with a carboxy-containing water-soluble mono-olefinic polymeric compound chemically bound with a hapten or a hapten which is chemically modified to bind it to said polymeric compound and (B-1) the antibody to said hapten; the components of said combination being physically separated from each other until used for determining the presence of a hapten in an assay sample.

3. An immunochemical assay reagent comprising a combination of (A-2) a hapten-supported latex obtained by chemically combining a polymeric latex having a particle diameter of about 0.01 to about 2 microns with a carboxy-containing water-soluble mono-olefinic polymeric compound chemically bound with a hapten or a hapten which is chemically modified to bind it to said polymeric compound and (B-2) the antibody to said hapten supported on a carrier, said carrier being sensitized or chemically bound with said hapten antibody; the components of said combination being physically separated from each other until used for determining the presence of a hapten in an assay sample.

4. A method for immunochemically determining a hapten in an assay sample which comprises contacting an assay sample containing a hapten with an immunochemical assay reagent which contains components capable of producing an agglutination reaction in the absence of a hapten but which agglutination reaction is inhibited in the presence of a hapten, said immunochemical assay reagent comprising a combination of (A-1) a carboxyl-containing water-soluble mono-olefinic polymeric compound chemically bound with a hapten or a hapten which is chemically modified to bind it to said polymeric compound and (B-2) the antibody to said hapten supported on a carrier, said carrier being sensitized or chemically bound with said hapten antibody; said components being used to determine the presence of a hapten corresponding to the hapten chemically bound to the polymeric component in the assay reagent in the above combination and wherein the components of said combination are separated from each other until contacted with said assay sample.

5. A method for immunochemically determining a hapten in an assay sample which comprises contacting an assay sample containing a hapten with an immunochemical assay reagent which contains components capable of producing an agglutination reaction in the absence of a hapten but which agglutination reaction is inhibited in the presence of a hapten, said immunochemical assay reagent comprising a combination of (A-2) a hapten-supported latex obtained by chemically combining a polymeric latex having a particle diameter of about 0.01 to about 2 microns with a carboxy-containing water-soluble mono-olefinic polymeric compound chemically bound with a hapten or a hapten which is chemically modified to bind it to said polymeric compound and (B-1) the antibody to said hapten; said components being used to determine the presence of a hapten corresponding to the hapten chemically bound to the polymeric component in the assay reagent in the above combination and wherein the components of said combination are separated from each other until contacted with said assay sample.

6. A method for immunochemically determining a hapten in an assay sample which comprises contacting an assay sample containing a hapten with an immunochemical assay reagent which contains components capable of producing an agglutination reaction in the absence of a hapten but which agglutination reaction is inhibited in the presence of a hapten, said immunochemical assay reagent comprising a combination of (A-2) a hapten-supported latex obtained by chemically combining a polymeric latex having a particle diameter of about 0.01 to about 2 microns with a carboxy-containing water-soluble mono-olefinic polymeric compound chemically bound with a hapten or a hapten which is chemically modified to bind it to said polymeric compound and (B-2) the antibody to said hapten supported on a carrier, said carrier being sensitized or chemically bound with said hapten antibody; said components being used to determine the presence of a hapten corresponding to the hapten chemically bound to the polymeric component in the assay reagent in the above combination and wherein the components of said combination are separated from each other until contacted with said assay sample.

* * * * *